United States Patent
Stinchcomb et al.

(10) Patent No.: US 10,022,366 B2
(45) Date of Patent: Jul. 17, 2018

(54) EXTENDING AND MAINTAINING MICROPORE VIABILITY OF MICRONEEDLE TREATED SKIN WITH LIPID BIOSYNTHESIS INHIBITORS FOR SUSTAINED DRUG DELIVERY

(71) Applicants: Audra L. Stinchcomb, Ruxton, MD (US); Priyanka Ghosh, Germantown, MD (US)

(72) Inventors: Audra L. Stinchcomb, Ruxton, MD (US); Priyanka Ghosh, Germantown, MD (US)

(73) Assignees: University of Maryland, Baltimore, Baltimore, MD (US); University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/786,698

(22) PCT Filed: Apr. 23, 2014

(86) PCT No.: PCT/US2014/035126
§ 371 (c)(1),
(2) Date: Oct. 23, 2015

(87) PCT Pub. No.: WO2014/176325
PCT Pub. Date: Oct. 30, 2014

(65) Prior Publication Data
US 2016/0074384 A1    Mar. 17, 2016

Related U.S. Application Data

(60) Provisional application No. 61/814,925, filed on Apr. 23, 2013.

(51) Int. Cl.
*A61K 31/44*     (2006.01)
*A61K 31/485*    (2006.01)
(Continued)

(52) U.S. Cl.
CPC .......... *A61K 31/485* (2013.01); *A61K 9/0014* (2013.01); *A61K 31/135* (2013.01); *A61K 31/341* (2013.01); *A61K 31/405* (2013.01)

(58) Field of Classification Search
CPC .. A61K 31/485; A61K 31/341; A61K 31/405; A61K 31/135; A61K 9/0014
(Continued)

(56) References Cited

U.S. PATENT DOCUMENTS

2009/0053673 A1    2/2009    Klabunde et al.
2011/0028905 A1    2/2011    Takada
(Continued)

OTHER PUBLICATIONS

Durstine et al, Pollock's Textbook of Cardiovascular Disease and Rehabilitation, 2008, p. 227 ( 3 pages).*
(Continued)

*Primary Examiner* — Taylor V Oh
(74) *Attorney, Agent, or Firm* — Eugene J. Molinelli; Beusse Wolter Sanks & Maire

(57) ABSTRACT

Microneedles and their use as a physical skin permeation enhancement technique facilitate drug delivery across the skin in therapeutically relevant concentrations. Micropores created in the skin by MNs reseal because of normal healing processes of the skin, thus limiting the duration of the drug delivery window. Pore lifetime enhancement strategies can increase effectiveness of MNs as a drug delivery mechanism by prolonging the delivery window. Fluvastatin (FLU) was used to enhance pore lifetime by inhibiting the synthesis of cholesterol, a major component of the stratum corneum lipids. The skin recovered within a 30-45-min time period following the removal of occlusion, and there was no significant irritation observed due to the treatment compared to the control sites. Thus, it can be concluded that localized skin treatment with FLU can be used to extend micropore (Continued)

lifetime and deliver drugs for up to 7 days across MN-treated skin.

29 Claims, 9 Drawing Sheets

(51) Int. Cl.
*A61K 31/135* (2006.01)
*A61K 31/341* (2006.01)
*A61K 31/405* (2006.01)
*A61K 9/00* (2006.01)

(58) Field of Classification Search
USPC .......................................................... 514/282
See application file for complete search history.

(56) References Cited

U.S. PATENT DOCUMENTS

2011/0245288 A1    10/2011  Stinchcomb et al.
2013/0041330 A1*   2/2013   Matsudo .............. A61K 9/0021
                                                  604/272

OTHER PUBLICATIONS

Brogden, Clinical evaluation of novel methods for extending microneedle pore lifetime, PhD. Thesis University of Kentucky. 2011, p. 1-181.*

Arora, A., et al., "Multicomponent chemical enhancer formulations for transdermal drug de-livery: More is not always better," J. Control Release, 2010, pp. 175-180, vol. 144.

Banks, S. L., et al., "Transdermal delivery of naltrexol and skin permeability lifetime after MN treatment in hairless guinea pigs," J. Pharm. Sci., 2010, pp. 3072-3080, vol. 99.

Banks, S., et al., "Diclofenac enables prolonged delivery of naltrexone through MN-treated skin," Pharm. Res., 2011, pp. 1211-1219, vol. 28.

Barry, B.W., "Mode of action of penetration enhancers in human skin," J. Control Release, 1987, pp. 85-97, vol. 6.

Brogden, N. K., et al., "Diclofenac delays micropore closure following MN treatment in human subjects," J. Control Release, 2012, pp. 220-229, vol. 163.

Brogden, N., et al., "Diclofenac enables unprecedented week-long MN-enhanced delivery of a skin impermeable medication in humans," Pharm. Res., 2013, pp. 1947-1955, vol. 30.

Elias, P.M., et al., "The potential of metabolic interventions to enhance transdermal drug delivery," J. Investig. Dermatol. Symp. Proc., 2002, pp. 79-85, vol. 7.

Ghosh, P., et al., "Development of a codrug approach for sustained drug delivery across MN-treated skin," J. Pharm. Sci., 2013, pp. 1458-1467, vol. 102.

Gill, H.S., et al., "Coated MNs for transdermal delivery," J. Control Release, 2007, pp. 227-237, vol. 117.

Grubauer, G., et al., "Lipid content and lipid type as determinants of the epidermal permeability barrier," J. Lipid Res., 1989, pp. 89-96, vol. 30.

Mao-Qiang, M., et al., "Optimization of physiological lipid mixtures for barrier repair," J. Investig. Dermatol., 1996, pp. 1096-1101, vol. 106.

Milewski, M., et al., "Vehicle composition influence on the MN-enhanced transdermal flux of naltrexone hydrochloride," Pharm. Res., 2011, pp. 124-134, vol. 28.

Paudel, K.S., et al., "Transdermal delivery of naltrexone and its active metabolite 6-beta-naltrexol in human skin in vitro and guinea pigs in vivo," J. Pharm. Sci., 2005, pp. 1965-1975, vol. 94.

Prausnitz, M.R., et al., "Transdermal drug delivery," Nat. Biotechnol., 2008, pp. 1261-1268, vol. 26.

Thong, H.Y., et al., "Percutaneous penetration enhancers: An overview," Skin Pharmacol. Physiol., 2007, pp. 272-282, vol. 20.

Tsai, J.C., et al., "Metabolic approaches to enhance transdermal drug delivery. 1. Effect of lipid synthesis inhibitors," J. Pharm. Sci., 1996, pp. 643-648, vol. 85.

Wermeling, D.P., et al., "MNs permit transdermal delivery of a skin-impermeant medication to humans," Proc. Natl. Acad. Sci. USA, 2008, pp. 2058-2063, vol. 105.

ISA/US, "International Search Report and Written Opinion for the corresponding PCT application US2014/35126", dated Nov. 24, 2014, pp. 1-17.

* cited by examiner

EXTENDING AND MAINTAINING MICROPORE VIABILITY OF MICRONEEDLE TREATED SKIN WITH LIPID BIOSYNTHESIS INHIBITORS FOR SUSTAINED DRUG DELIVERY

CROSS-REFERENCE TO RELATED APPLICATIONS

This application is a 371 national stage application of PCT Application No. PCT/US2014/35126, filed Apr. 23, 2014, and claims the benefit of U.S. Provisional Application No. 61/814,925, filed on Apr. 23, 2013; the entire contents of which are hereby incorporated by reference as if fully set forth herein.

BACKGROUND

The delivery of drugs to a patient is conventionally performed in a number of different ways. For example, intravenous delivery is by injection directly into a blood vessel; intraperitoneal delivery is by injection into the peritoneum; subcutaneous delivery is under the skin; intramuscular delivery is into a muscle; and oral delivery is through the mouth. The stratum corneum is a tough, scaly layer made of dead cell tissue that extends around 10-20 microns from the skin surface and has no blood supply. Because of the density of this layer of cells, moving compounds across the skin, either into or out of the body, can be very difficult.

Current techniques for delivering local pharmaceuticals through the skin include methods that use needles or other skin piercing devices and methods that do not use such devices. Invasive procedures, such as use of needles or lances, can effectively overcome the barrier function of the stratum corneum. However, these methods suffer from several major disadvantages, including pain, local skin damage, bleeding, risk of infection at the injection site, and creation of contaminated needles or lances. These methods also usually require a trained administrator and are not suitable for repeated, long-term, or controlled use.

MNs ("MNs") are an alternative technique used to permeabilize the stratum corneum (hereinafter "SC") barrier and increase the number of drugs that can be delivered transdermally. The MNs are similar to larger conventional medical needles, so that drug compounds may be delivered through the shaft and into the skin. The skin is a self-regulatory organ and employs different methods for recovery after assault. Skin wound healing consists of multiple phases, inflammatory response being the first step. Transdermal patch occlusion helps to delay the recovery process. However, micropores created by MNs begin to close between 48-72 hours for the specific MN geometry.

As such, a need currently exists for a transdermal MN device that can easily deliver a drug compound for a 7-day period. Therefore, in order to develop a 7-day transdermal drug delivery system, pore lifetime enhancement techniques need to be employed in order to allow for continued skin permeation. Lipid biosynthesis inhibitors such as HMG-CoA reductase inhibitors can be used to delay the normal healing process thus enhancing micropore lifetime and pore viability. By combining the transdermal drug with a lipid biosynthesis inhibitor such as fluvastatin (a HMG CoA reductase inhibitor) ("FLU") or other compound, which inhibits the biosynthesis of cholesterol, a lipid component of skin, the skin recovery process can be improved. This skin recovery inhibition helps to extend and maintain the lifetime of the skin micropores and allow sustained delivery of a drug transdermally.

SUMMARY OF THE INVENTION

In certain embodiments, transdermal drug delivery systems and methods for making them are provided. The transdermal drug delivery system contains an array of MNs and a lipid biosynthesis inhibitor. The transdermal drug delivery system can further include an active pharmaceutical agent. Preferably, the lipid biosynthesis inhibitor is a HMG-CoA reductase inhibitor selected from the group consisting of atorvastatin, fluvastatin, pitavastatin, pravastatin, rosuvastatin, and simvastatin. Preferably the active pharmaceutical agent is a µ-opioid receptor antagonist, preferably NTX.

Embodiments are also directed to pharmaceutical compositions and kits containing them that contain one or more lipid biosynthesis inhibitors or derivatives thereof, preferably FLU, and an active pharmaceutical agent such as a µ-opioid receptor antagonist, preferably NTX preferably, where the active pharmaceutical agent is transdermally delivered by use of MNs that may be coated for reduction or treatment of diseases such as opioid and alcohol addiction. Methods are provided for contacting the skin with an array of MNs and applying these pharmaceutical compositions.

In certain embodiments, methods are provided for enhancing the lifetime or pore viability of micropores in the skin and ultimately sustaining delivery of a transdermally delivered drug in a patient in need thereof. First, the skin of the patient in need thereof is contacted with a MN device such as a solid adhesive patch containing 50 solid stainless steel MNs arranged in 5×10 arrays of MNs to generate a first set of micropores. Then, the MN device is rotated at an angle following the first insertion in the skin of the patient to generate a second set of non-overlapping micropores. Preferably the angle is about 45 degrees. Upon generation of non-overlapping micropores, the MN-treated skin is topically pretreated with a lipid biosynthesis inhibitor such as a HMG-CoA reductase inhibitor (e.g., atorvastatin, fluvastatin, pitavastatin, pravastatin, rosuvastatin, and simvastatin) to enhance micropore lifetime or pore viability in the MN-treated skin. Then, a therapeutically effective amount of a active pharmaceutical agent such as a µ-opioid receptor antagonist (e.g., NTX) is administered on the MN-treated skin. An occlusive dressing is applied for up to 7 days wherein drug delivery in the MN-treated skin of a patient is sustained at therapeutically effective plasma concentrations up to a period of about 7 days.

In other embodiments, methods are provided for reducing or treating opioid or alcohol addiction in a patient in need thereof. As described above, the skin of the patient is contacted with a MN device such as a solid adhesive patch containing 50 solid stainless steel MNs arranged in 5×10 arrays of MNs to generate a first set of micropores. Then, the MN device is rotated at an angle following the first insertion in the skin of the patient to generate a second set of non-overlapping micropores. Preferably the angle is about 45 degrees. Upon generation of non-overlapping micropores, the MN-treated skin is topically pretreated with a lipid biosynthesis inhibitor such as a HMG-CoA reductase inhibitor (e.g., atorvastatin, fluvastatin, pitavastatin, pravastatin, rosuvastatin, and simvastatin) to enhance micropore lifetime or pore viability in the MN-treated skin. Then, a therapeutically effective amount of a active pharmaceutical agent such as a µ-opioid receptor antagonist (e.g., buprenorphine/naloxone, cyprodime, Depade, morphine, naltrexone HCL, ReVia, suboxone, vivitrol, and zylosolv) is administered on the MN-treated skin and repeated if necessary. An occlusive dressing is applied for up to 7 days wherein the μ-opioid receptor antagonist such as NTX in the MN-treated skin of a patient is sustained at therapeutically effective plasma concentrations up to a period of about 7 days.

Other embodiments include kits that comprise transdermal drug delivery systems that comprise, a lipid biosynthesis inhibitor such as a HMG-CoA reductase inhibitor (e.g., FLU) to enhance micropore lifetime or pore viability in the skin. The kit may further comprise a therapeutically effective active pharmaceutical agent such as a μ-opioid antagonist (e.g., NTX), and an occlusive dressing.

In certain embodiments, abuse-resistant patches and methods of making them are provided. The abuse-resistant patch includes a backing layer; a first layer underlying the backing layer, the first layer comprising: an opioid antagonist or opioid antagonist prodrug which is not transdermally delivered at therapeutic levels when the patch is used for transdermally administering the opioid to the subject; wherein the backing layer is substantially impermeable to the opioid antagonist or opioid antagonist prodrug of the second layer; a second layer underlying the first layer, the third layer comprising: (i) a lipid biosynthesis inhibitor; (ii) an opioid antagonist; (iii) a pressure sensitive adhesive; wherein the third layer is adapted to be in diffusional communication with the skin of the subject to transdermally administer a therapeutically effective amount of the opioid antagonist to the subject; and a barrier layer located between the first and second layer, the barrier layer comprising: a water-insoluble polymeric material and a water-soluble polymer; wherein the release ratio is between about 1:60 and about 60:1 after the patch has been placed in ethanol, water, or a phosphate buffer having a pH of about 6.5 for greater than about 30 seconds.

These and other features, aspects, and advantages of the present invention will become better understood with regard to the following description, appended claims, and accompanying figures.

BRIEF DESCRIPTION OF THE DRAWINGS

The following figures form part of the present specification and are included to further demonstrate certain embodiments. Embodiments may be better understood by reference to one or more of these drawings in combination with the detailed description of specific embodiments presented herein.

DETAILED DESCRIPTION

1. Definitions

Figure 1A:
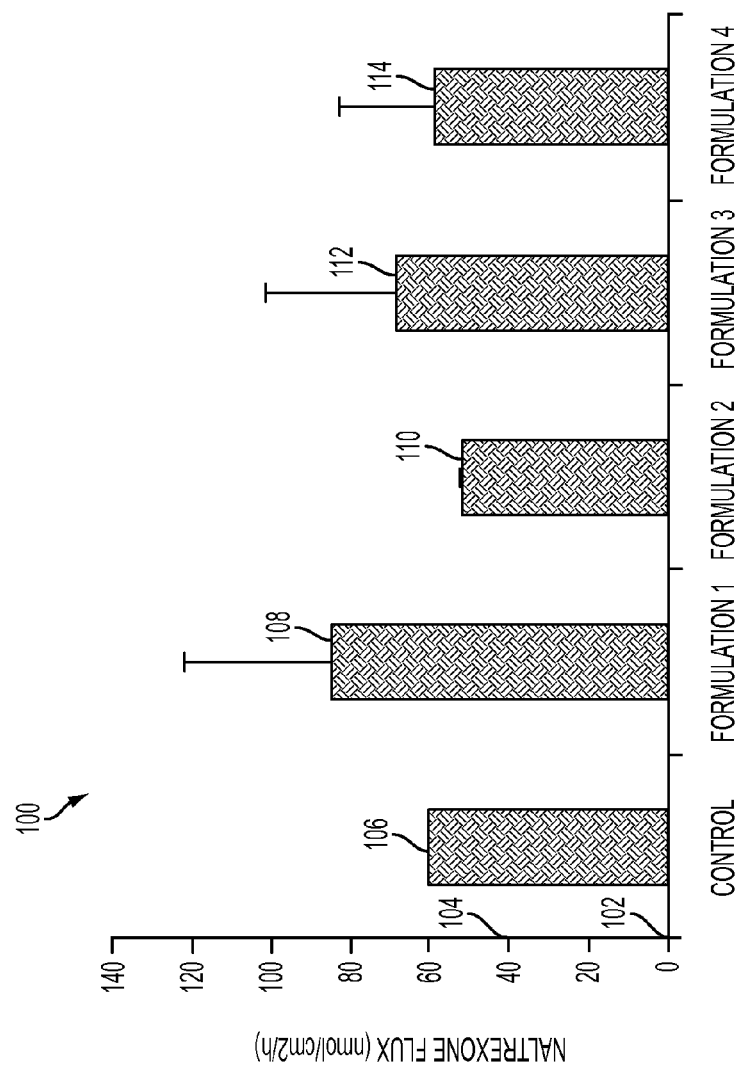
FIG. 1A-1B are bar graphs that show formulation optimization for application of FLU along with NTX gel according to an embodiment.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors, McGraw-Hill/Appleton & Lange: New York (2000). Unless defined otherwise, all technical and scientific terms used herein have the same meaning as commonly understood by one of ordinary skill in the art.

As used in this specification and the appended claims, the singular forms "a," "an," and "the" encompass embodiments having plural referents, unless the content clearly dictates otherwise. As used in this specification and the appended claims, the terms "or" is generally employed in its sense including "and/or" unless the content clearly dictates otherwise.

As used herein the terms "abuse resistant" and "abuse deterrent" are synonymous and shall mean any pharmaceutical composition, formulation or dosage form that when misused, prevents the abuser from achieving the non-therapeutic effects sought from misuse of the composition, formulation or dosage form, such as opioid induced euphoria.

The term "active pharmaceutical agent" is an agent, including any chemical, protein, peptide, or nucleotide, that is administered to a mammal in order to achieve a desired therapeutic result. Examples of active pharmaceutical agents can be found in The Merck Index: An Encyclopedia of Chemicals, drugs, and Biologicals, 14$^{th}$ Edition; Goodman & Gilman's The Pharmacological Basis of Therapeutics, 11th Edition; Physicians Desk Reference 2008, 62 Edition; Remington's Pharmaceutical Sciences, 16th Edition, which are incorporated herein by reference. In one embodiment, the active pharmaceutical agent is an opioid μ-opioid antagonist, preferably NTX.

As used herein, "administering" an active pharmaceutical agent may be performed using any of the various methods or delivery systems well known to those skilled in the art. The preferred method for administering HMG-CoA reductases inhibitors or μ-opioid antagonists is topical/transdermal administration directly to the skin.

The terms "animal," "patient," or "subject," as used herein, mean any animal (e.g., mammals, including but not limited to humans, primates, dogs, cattle, cows, horses, kangaroos, pigs, sheep, goats, cats, rabbits, rodents, and transgenic non-human animals) that is to be the recipient of a particular treatment. Typically, the terms "animal," "subject," and "patient" are used interchangeably herein in reference to a human subject or a rodent. The preferred animal, patient, or subject is a human.

The terms "codrug" or mutual "prodrug" as used herein mean two synergistic drugs chemically linked together, in order to improve the drug delivery properties of one or both drugs. The constituent drugs are indicated for the same disease, but may exert different therapeutic effects via disparate mechanisms of action. An effective codrug should be pharmacologically inactive in its own right, but should release the constituent drugs upon biochemical breakage of the chemical linkage at the target tissue where their therapeutic effects are needed. As such, the chemical linkage (usually a covalent bond) should be subjectable to biodegradation, such as hydrolysis, by an enzymatic or non-enzymatic mechanism. The differential distribution of enzymes capable of catalyzing the breakage of the chemical linkage in different tissues may be exploited to achieve tissue-specific metabolism of the codrug to release the constituent drugs. Lipid biosynthesis inhibitors in certain embodiments as described herein include 5-(tetradecycloxy)-2-furacarboxylic acid (TOFA) for fatty acid synthesis, codrugable with a water solubilizing bridge moiety; fluvastatin (FLU) for cholesterol synthesis, potentially codrugable without a bridge moiety; and β-chloralanine (BCA) for ceramide synthesis, codrugable with an acyloxymethyloxy bridge moiety.

The term "kit," as used herein, means any manufacture (e.g., a package or container) comprising a MN device and at least one lipid biosynthesis inhibitor reagent, e.g., a HMG-CoA reductase inhibitor for enhancing micropore lifetime for enhancement of drug delivery across MN-treated skin. The kit can further comprise a μ-opioid antagonist for treatment of or reduction of opioid or alcohol addiction and an occlusive dressing. In certain embodiments, the manufacture may be promoted, distributed, or sold as a unit for performing the methods of the present invention.

The terms "lipid biosynthesis inhibitor" or "biochemical enhancer," as used herein, refer to a chemical agent employed to prevent the synthesis of the essential lipids required for lamellar body synthesis and thus the proper formation of the stratum corneum. Local concentrations of specific inhibitors of the three lipid synthesis pathways—namely cholesterol, fatty acids and ceramides—can be used to alter the molar ratio and delay barrier recovery. Some of the inhibitors in certain embodiments of the invention include, but are not limited to, 5-(tetradecycloxy)-2-furancarboxylic acid (TOFA) for fatty acid synthesis, fluvastatin (FLU) for cholesterol synthesis, and β-chloralanine (BCA) for ceramide synthesis.

The term "MN" or "MN," as used herein, means a device to breach the stratum corneum barrier function in order to facilitate effective transport of molecules across the skin. This device involves use of micron-sized needles fabricated of different materials and geometries to create transient aqueous conduits across the skin. MNs, alone or with other enhancing strategies, have been demonstrated to dramatically enhance the skin permeability of numerous therapeutic molecules including biopharmaceuticals either in vitro, ex vivo or in vivo experiments. In a preferred embodiment, solid stainless steel MNs were used to permeabilize the skin and do not remain in contact with the skin thereafter. A "MN array" may be fabricated to produce patches containing 50 MNs arranged in 5×10 arrays of MNs. There are a number of different types of MNs and application techniques. Solid MNs are used to permeabilize the skin followed by application of drug over treated skin, or drug coated onto the MN itself. Polymer MN's are used to load drug into the polymer itself for delivery. Hollow MN's are used in conjunction with an infusion pump to facilitate delivery of hormones and vaccines over short periods of time.

The term "occlusive dressing" as used herein means a first aid application that literally provides a complete barrier around and over the wound. This seal prevents air, water, and contaminants from getting into the wound or on the surrounding tissue. This dressing has traditionally been used with large wounds, particularly to the chest or abdominal area, to provide immediate control of pressure and bleeding. Occlusive dressings are now also used in less serious wound treatment, including minor superficial types of wounds. By using occlusive wound dressing to enclose the wound, there is no risk of infection or contact with pathogens during the healing process and the area is kept secure and more protected. This in turn results in a shorter overall healing time and much less chance of significant or even minimal scarring. Occlusive dressings can often be used in combination with hydrogels, hydrocolloids and films that trap moisture close to the wound while still providing that tight seal required for effective healing.

As used herein an "opioid" refers to compounds that affect opiate receptors, such as the mu, kappa, delta, epsilon, iota, lambda and zeta receptors and includes compounds and substances which activate opiate receptors ("opioid agonists"), inactivate or block opiate receptors ("opioid antagonist") and partially activate and partially inactivate or block opiate receptors ("opioid agonist-antagonists"). The term opioid also includes natural opiates, semi-synthetic opiates, fully synthetic opioids and endogenous opioid peptides, as well as prodrugs of such compounds. The term opioid also includes any pharmacologically acceptable salts of an opioid.

"Pharmaceutically acceptable salts," or "salts," include the salts of opioids suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, tosylic, pamoic, napsylic, hydrobromic, valeric, oleic, lauric, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, beta-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of opioids may be prepared.

The term "pore viability," as provided herein, means pores, holes or channels created by the entry of one or more MNs into the skin of a mammal in need of transdermal administration of an active pharmaceutical agent and the duration of lifetime that the resulting pores remain sufficiently open or "un-healed" thereby allowing the transdermal delivery of an active pharmaceutical agent to be systemically or locally delivered, whereby the dosing interval between MN treatments can be extended.

As used herein, "prodrug" refers to a pharmacologically inactive (or significantly less active) chemical derivative that can be converted, enzymatically or non-enzymatically, in vivo or in vitro, to an active drug molecule, which is capable of exerting one or more physiological effects.

The term "statin" or "HMG-CoA reductase inhibitor," as used herein, means a class of drugs used to lower cholesterol levels by inhibiting the enzyme HMG-CoA reductase, which plays a central role in the production of cholesterol in the liver, which produces about 70 percent of total cholesterol in the body. As of 2010, a number of statins are on the market: atorvastatin (Lipitor®), fluvastatin (Lescol®), lovastatin (Mevacor®, Altocor®), pitavastatin (Livalo®), pravastatin (Pravachol®), rosuvastatin (Crestor®) and simvastatin (Zocor®). Several combination preparations of a statin and another agent, such as ezetimibe/simvastatin, are also available.

The term "transdermal flux" means the rate of passage of any agent in and through the skin of an individual or the rate of passage of any analyte out through the skin of an individual.

The term "transdermal" means the delivery or extraction of an agent through the skin.

The term "transdermal drug" or "transdermally delivered drug," as used herein, means a drug's route of administration wherein active ingredients are delivered across the skin for systemic distribution. In preferred embodiments of the invention, a drug that is transdermally delivered across the MN-treated skin may include, but is not limited to: buprenorphine, clonidine, estradiol, estradiol and levonorgestrel, estradiol and norethindrone acetate, ethinyl estradiol and norelgestromin, fentanyl, granisetron, insulin, methylphenidate, naltrexone HCL, nicotine, nitroglycerin, oxybutynin, oxybutynin chloride, rivastigmine, scopolamine, selegiline, sumatiptan succinate, testosterone, capsaicin, diclofenac epolamine, diclofenac sodium, lidocaine, lidocaine and prilocaine, lidocaine and tetracaine, methylphenidate, menthol and capsaicin, menthol and methyl salicylate, salicylic acid, rivastigmine, rotigotine, and trolamine salicylate.

The term "therapeutically effective amount" as used herein means an amount that achieves the intended therapeutic effect of reducing or treating opioid or alcohol addiction in a patient in need thereof. The full therapeutic effect does not necessarily occur by administration of one dose and may occur only after administration of a series of doses. Thus, a therapeutically effective amount may be administered in one or more administrations per day for successive days.

The term "treating" a disease including but not limited to opioid or alcohol addiction in a patient, as used herein, means taking steps to obtain beneficial or desired results, including clinical results. For purposes of this invention, beneficial or desired clinical results include but are not limited to alleviation or amelioration of one or more symptoms of opioid or alcohol addiction; diminishing the extent of disease; delaying or slowing disease progression; amelioration and palliation or stabilization of the disease state.

The terms "treat" or "treatment," as used herein, mean both therapeutic treatment and prophylactic or preventative measures, wherein the object is to prevent or slow down (lessen) an undesired physiological change or disorder, such as the development, progression, or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having opioid or alcohol addiction.

2. Overview

It has been discovered that lipid biosynthesis inhibitors such as the HMG-CoA reductase inhibitor (e.g., FLU) can be used to delay resealing of micropores prolonging pore viability and sustain drug delivery (e.g., NTX) across MN-treated skin. It has further been discovered that quantifiable mean plasma concentrations of drugs transdermally delivered after HMG-CoA reductase inhibitor treatment are maintained at a therapeutically effective amounts for up to 7 days.

Figure 1B:
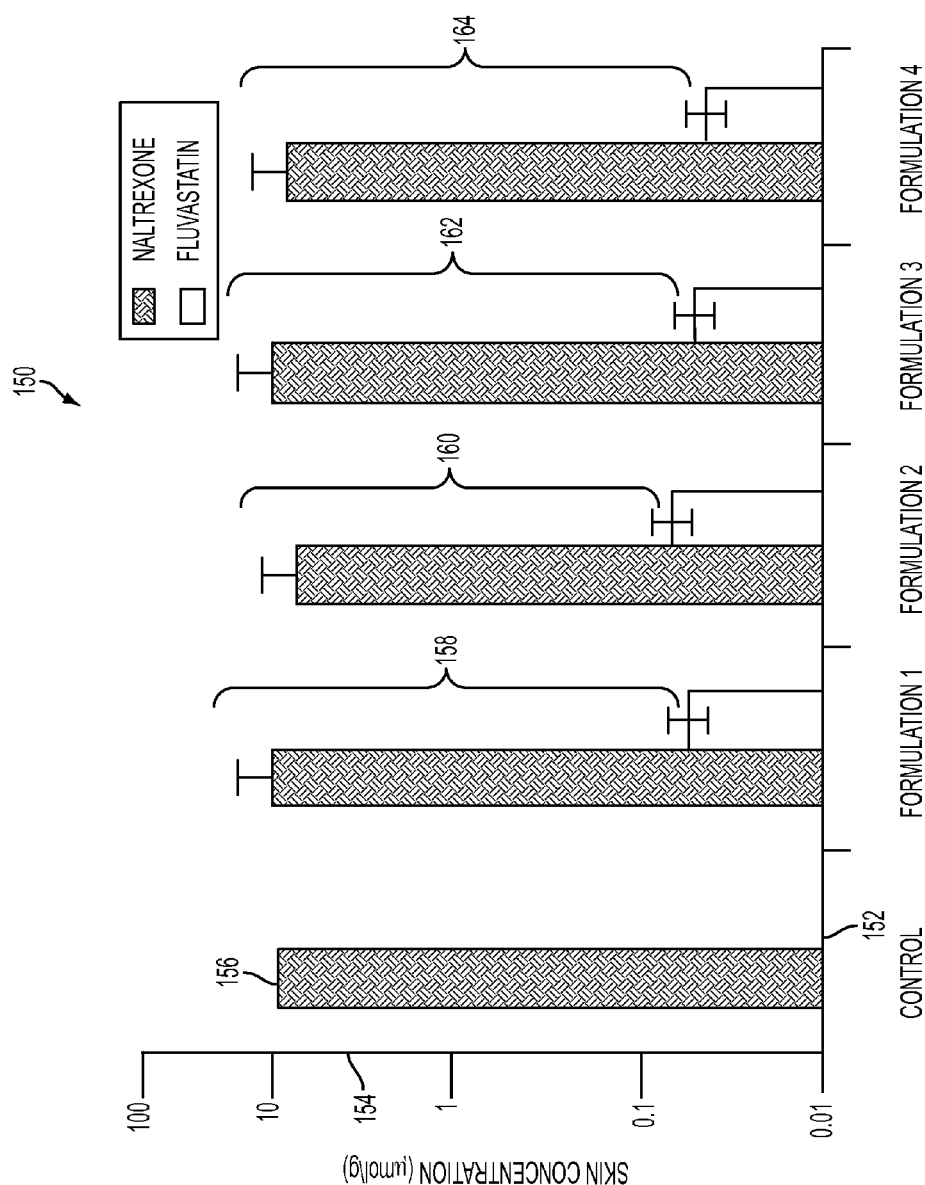

FIG. 1A-1B are bar graphs 100 and 150 that illustrate example formulation optimization for application of FLU along with NTX gel, according to an embodiment. FIG. 1A is a bar graph 100 that shows flux of NTX across MN-treated skin and includes a horizontal axis 102 that represents a control 106, FLU in 200 proof ethanol (formulation 1) 108, acetone (formulation 2) 1110, PG-ethanol=7:3 (formulation 3) 112, and PG-ethanol-water=1:2:1 (formulation 4) 114 and a vertical axis 104 that indicates naltrexone flux in nmol/cm2/h. FIG. 1B is a bar graph 150 that has a horizontal axis 152 that represents a control 156, FLU in 200 proof ethanol (formulation 1) 158, acetone (formulation 2) 160, PG-ethanol=7:3 (formulation 3) 162, and PG-ethanol-water=1:2:1 (formulation 4) 164 and a vertical axis 154 that illustrates skin concentration of NTX in µmol/g and FLU across MN-treated skin. n≥3 for all studies except control NTX. p>0.05 for flux and skin concentration data among all groups.

Figure 2A:
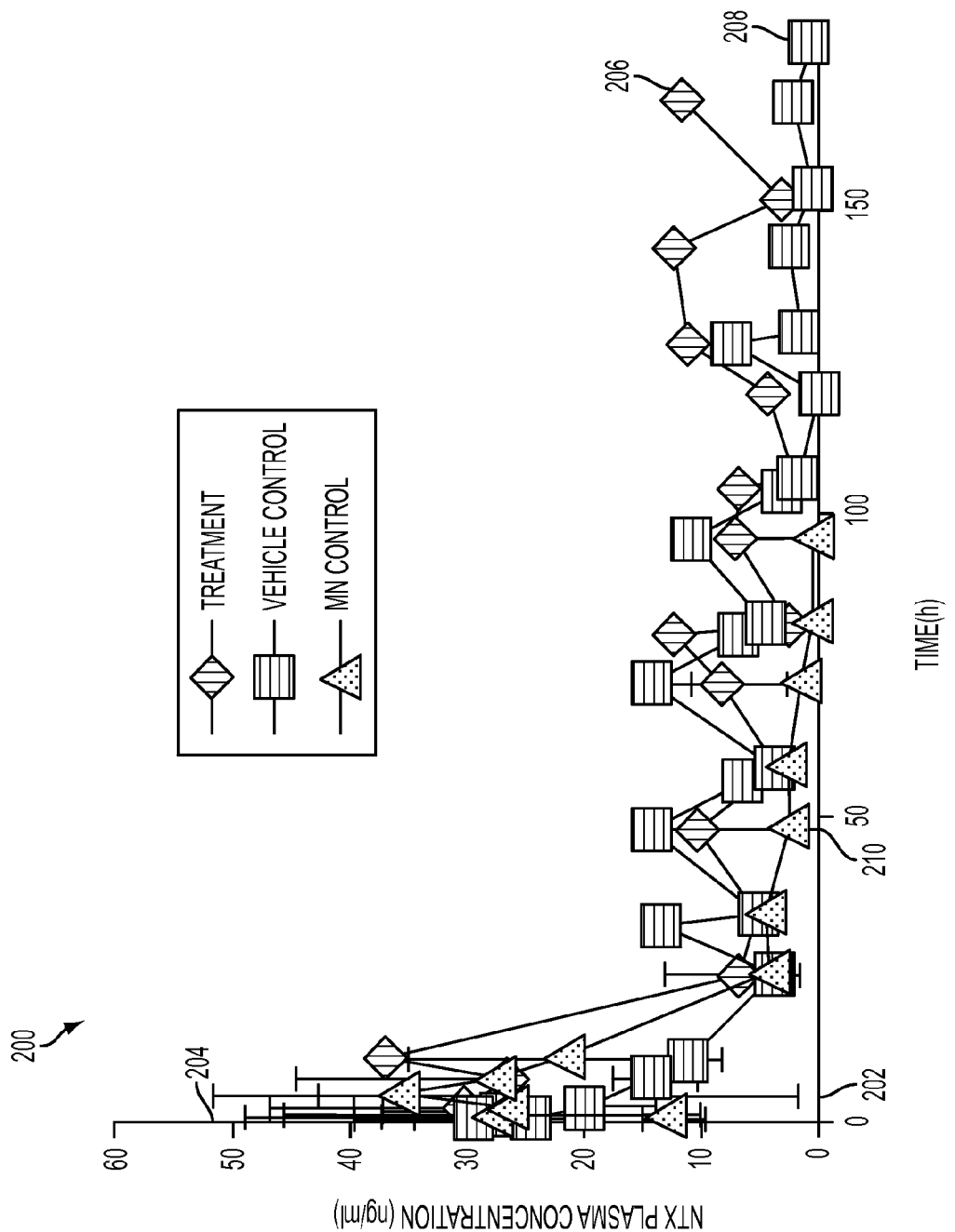
FIG. 2A-2B are graphs that illustrate NTX plasma concentrations in HGP following application of MN and FLU, MN and vehicle control or MN only according to an embodiment.
Figure 2B:
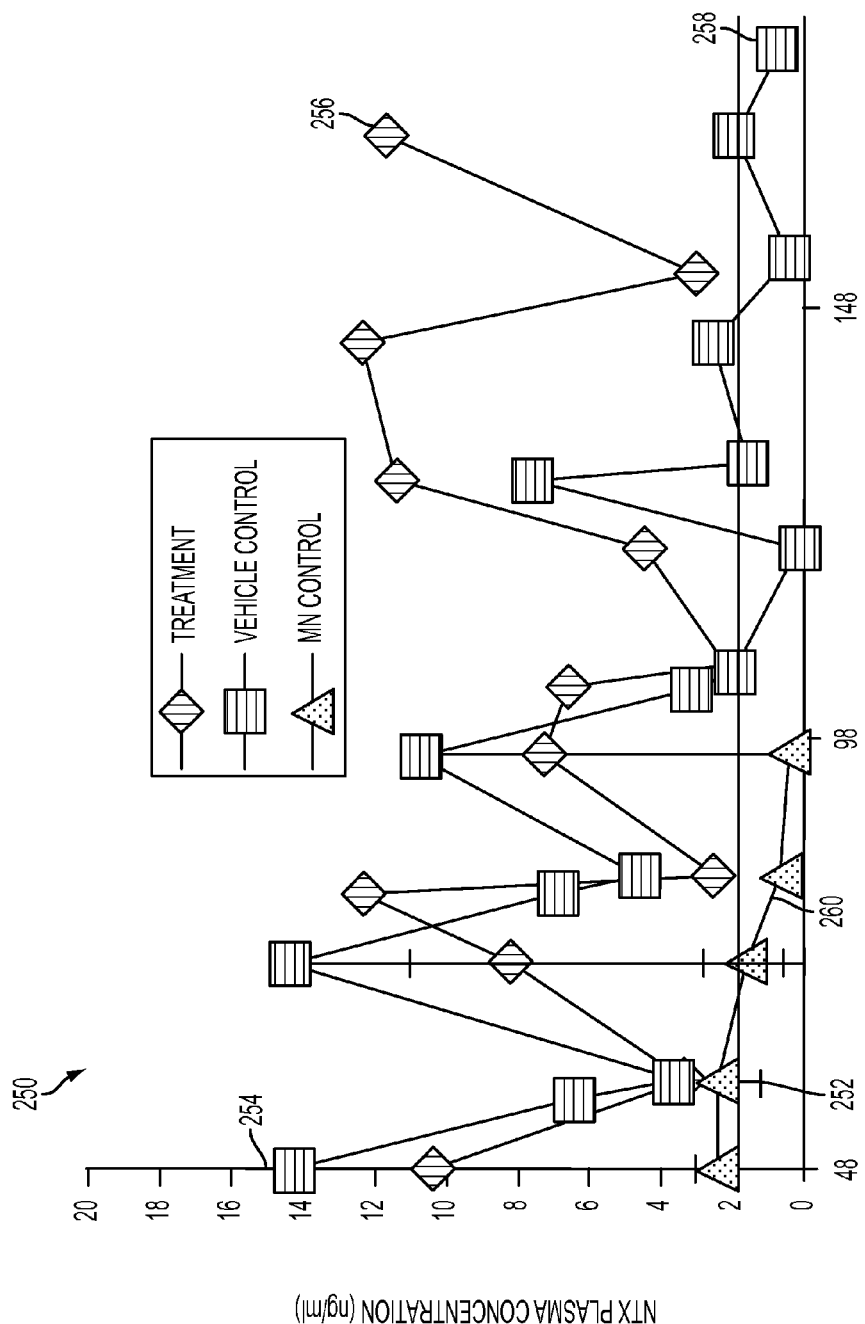

FIG. 2A-2B are graphs that illustrate NTX plasma concentrations in HGP following application of MN and FLU, MN and vehicle control or MN only according to an embodiment. FIG. 2A-2B are graphs 200 and 250 that illustrate NTX plasma concentrations in HGP following application of MN and FLU, MN and vehicle control or MN only, according to an embodiment. FIG. 2A is a graph 200 that has a horizontal axis 202 that reflects time periods at 50, 100, and 150 hours and a vertical axis 204 that shows NTX plasma concentration in ng/mL following application of MN and FLU 206, MN and ethanol vehicle control 208, or MN only 210. FIG. 2B is a graph 250 that has a horizontal axis 252 that reflects time periods at 48, 98, and 148 hours and a vertical axis 254 that shows NTX plasma concentration in ng/ML following application of MN and FLU 256, MN and ethanol vehicle control 258, or MN only 260. n≥3 for all studies.

Figure 3:
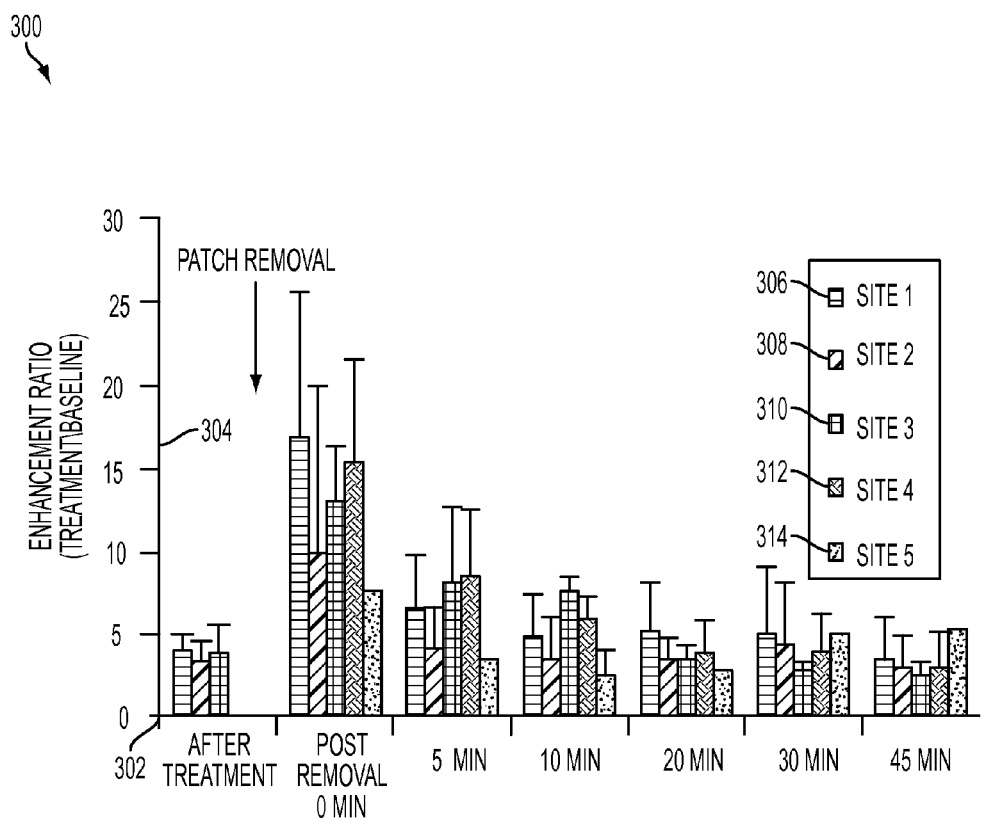
FIG. 3 is a bar graph that illustrates recovery of skin following 7-day treatment with FLU using transepidermal water loss (hereinafter "TEWL") according to an embodiment.

FIG. 3 is a bar graph that illustrates recovery of skin following 7-day treatment with FLU using TEWL according to an embodiment. FIG. 3 is a bar graph 300 that illustrates recovery of skin following 7-day treatment with FLU using TEWL having a horizontal axis 302 showing time periods after MN treatment, after removal at 0 min, at 5 min, at 10 min, at 20 min, at 30 min, and at 45 min and having a vertical axis 304 showing the enhancement ration as treatment/baseline. Measurements were obtained before, immediately following treatment, and after removal of patches at 7 days for site 1: MN+NTX gel+FLU (200 proof ethanol), 306, for site 2: MN+NTX gel+200 proof ethanol, 308, for site 3: MN+placebo gel, 310, for site 4: no MN treatment+placebo gel, 312, and for site 5: occlusion only, 314. n=3. Data are presented as a ratio of TEWL enhancement over baseline. $p>0.05$ among all sites.

Figure 4:
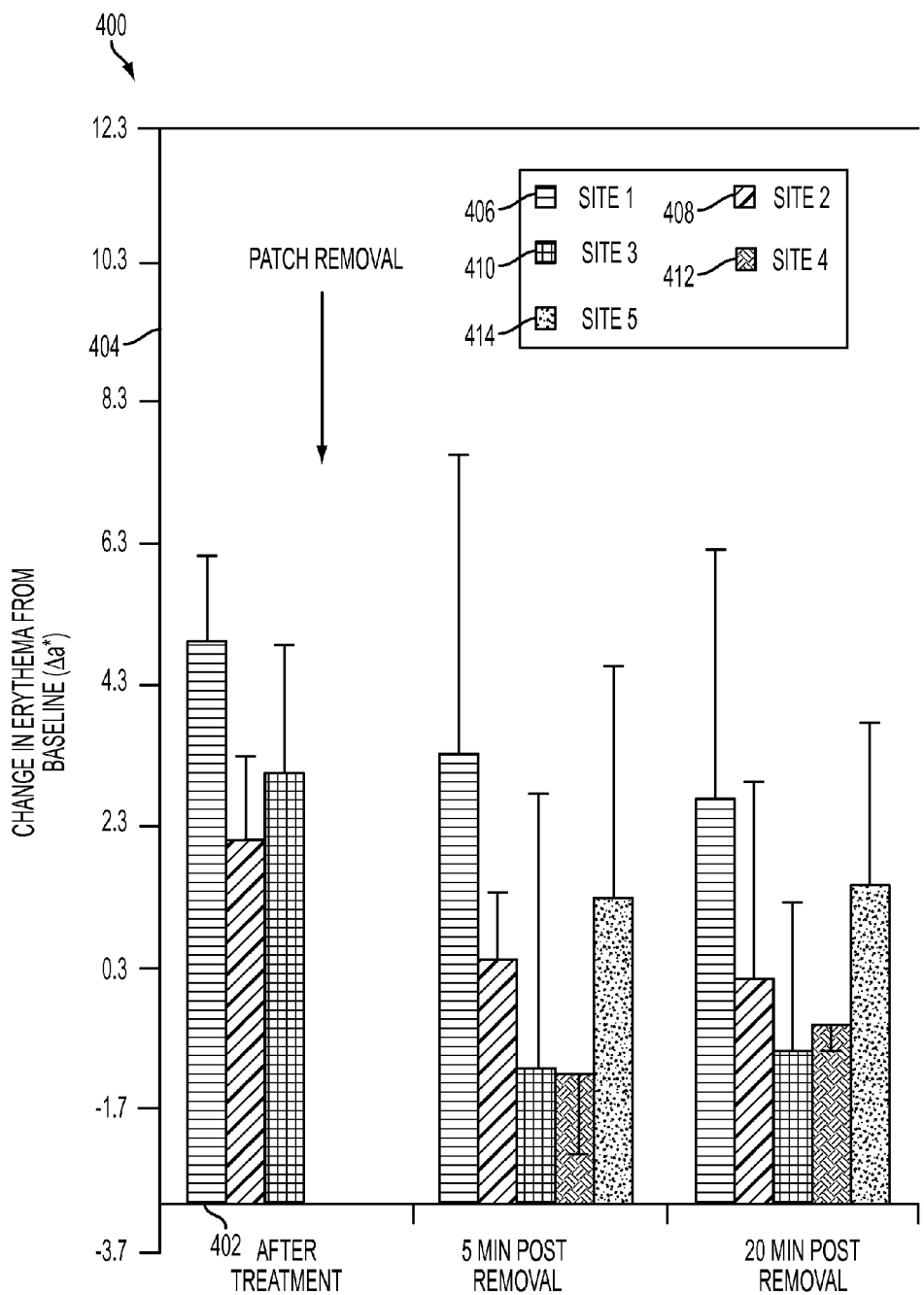
FIG. 4 is a bar graph that illustrates change in erythema of the skin following 7-day treatment with FLU using colorimetry according to an embodiment.

FIG. 4 is a bar graph 400 that illustrates change in erythema of the skin following 7-day treatment with FLU using colorimetry according to an embodiment. FIG. 4 illustrates the change in erythema of the skin following 7-day treatment with FLU using colorimetry. FIG. 4 has a horizontal axis 402 showing measurements obtained immediately following MN treatment, and fat 5 minutes and 20 minutes after patch removal at 7 days for site 1: MN+NTX gel+FLU (200 proof ethanol), 406, for site 2: MN+NTX gel+200 proof ethanol, 408, for site 3: MN+placebo gel, 410, for site 4: no MN treatment+placebo gel, 412, and for site 5: occlusion only, 414 and a vertical axis 404 showing change in erythema. Data are presented as change in erythema from baseline, $p>0.05$ among all sites.

Figure 5:
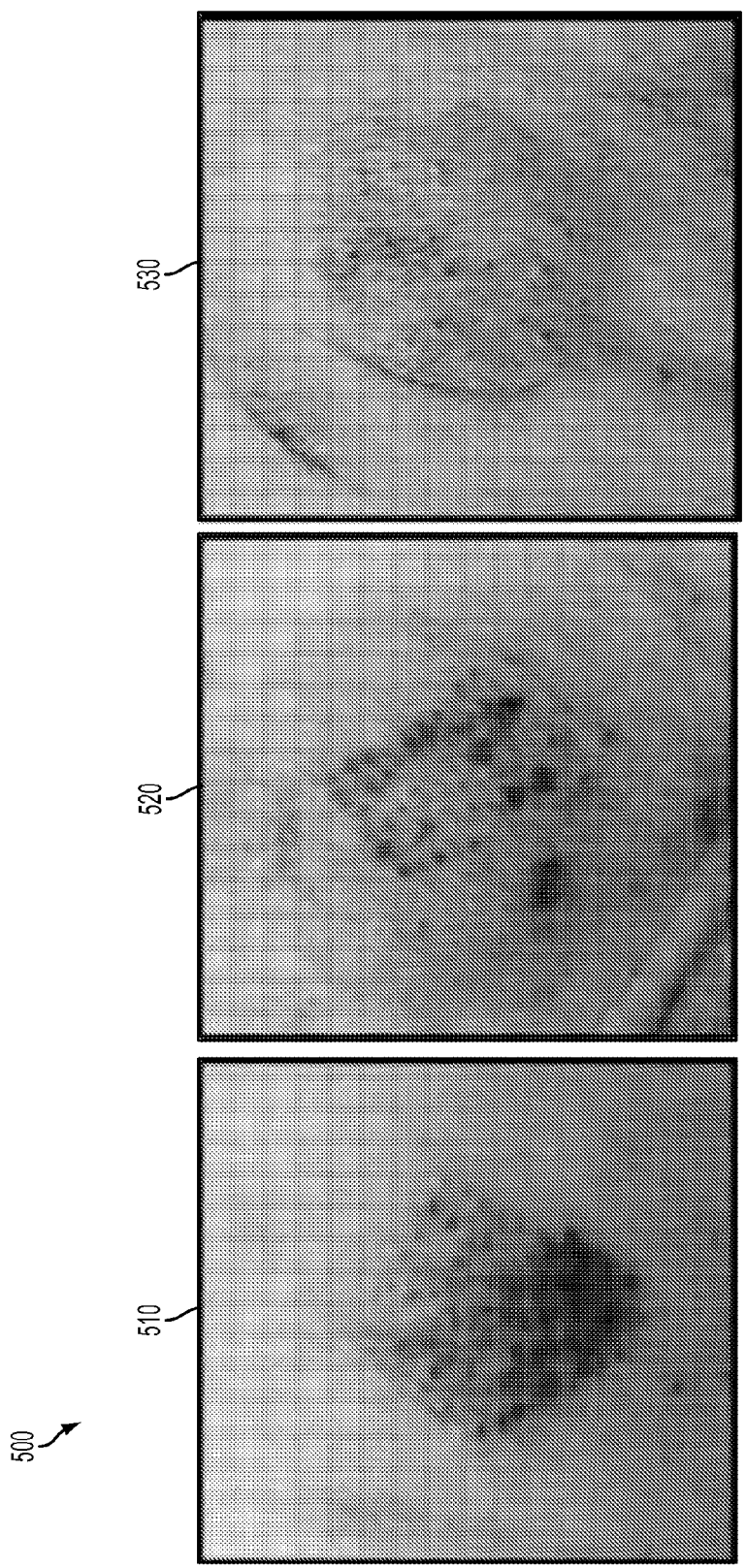
FIG. 5A-5C are photographs that illustrate Gentian violet staining in HGP at 7 days following treatment with 1.5% FLU in 200 proof ethanol according to an embodiment.

FIG. 5 is a photograph that illustrates Gentian violet staining in HGP at 7 days following treatment with 1.5% FLU in 200 proof ethanol according to an embodiment. FIG. 5A-5C 500 are photographs 510, 520, and 530 that illustrate Gentian violet staining in HGP at 7 days following treatment with 1.5% FLU in 200 proof ethanol 510 and 520 or 200 proof ethanol only 530. The images show that pores can be visualized at 7 days following FLU treatment in HGP, whereas staining of pores cannot be visualized in the ethanol control.

Figure 6:
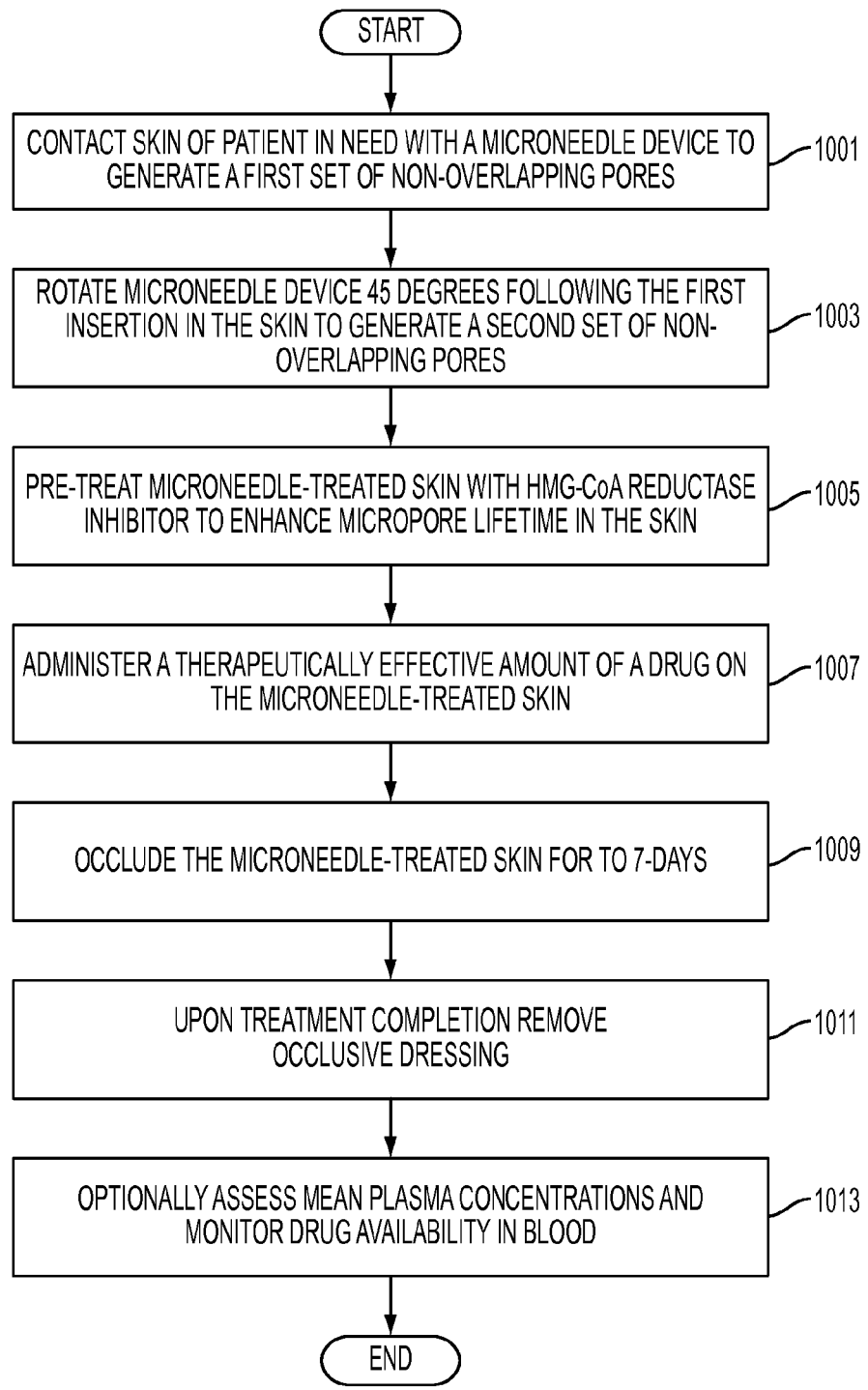
FIG. 6 is a flow chart that illustrates an example method for extending the lifetime of a transdermally delivered drug in a patient in need thereof, according to an embodiment.

FIG. 6 is a flow chart that illustrates an example method for extending the lifetime of a trandermally delivered drug in a patient in need thereof, according to an embodiment. Although steps are shown in FIG. 6 as integral blocks in a particular order for purposes of illustration, in other embodiments one or more steps or portions thereof may be performed in a different order, or overlapping in time, in series or in parallel, or one or more steps or portions thereof may be omitted, or additional steps added, or the process may be changed in some combination of ways.

In step 1001, the skin of the patient in need thereof is contacted with a MN device to generate a first set of micropores. In step 1003, the MN device is rotated 45 degrees following the first insertion in the skin of the patient in need thereof to generate a second set of non-overlapping pores. If it is determined that the patient has a sufficient amount of non-overlapping pores, in step 1005, the MN-treated skin is topically pre-treated with a lipid biosynthesis inhibitor such as a HMG-CoA reductase inhibitor to enhance micropore lifetime in the skin. In step 1007, a therapeutically effective amount of a drug is administered on the MN-treated skin. If the HMG-CoA reductase inhibitor and effective amount of drug are successfully administered on the MN-treated skin, then in step 1009, the MN-treated skin is occluded for up to 7 days. Upon completion of the treatment, in step 1011, the occlusive dressing is removed. In an optional step 1013, mean plasma concentrations may be obtained to assess and monitor drug availability in the blood.

Figure 7A:
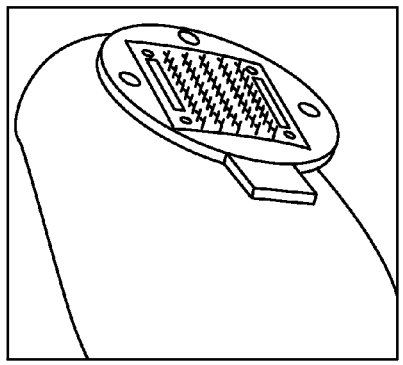
FIG. 7A-7C are photographs that illustrate a MN patch for delivery and human skin after insertion of the MN patch according to an embodiment.
Figure 7B:
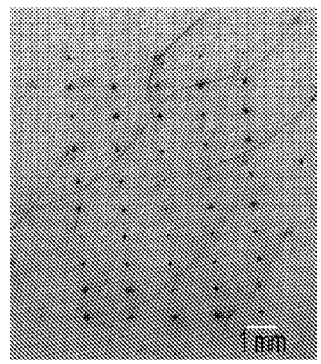
Figure 7C:
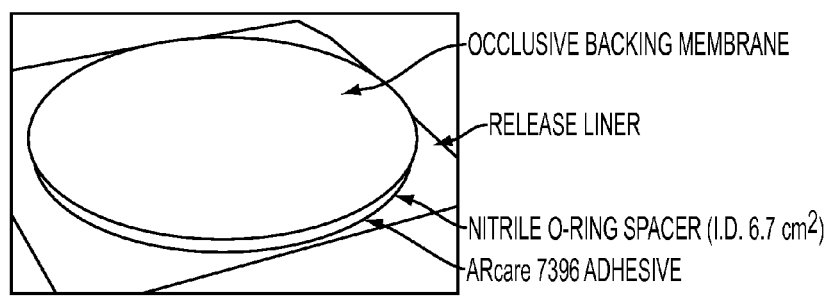

FIG. 7A-7C are photographs that illustrate a 50-MN patch resting on the tip of a human thumb (FIG. 7A), an image of human skin after insertion of the 50-MN patch and staining with gentian violet, a dye that selective stained sites of skin perforation (FIG. 7B), and a NTX transdermal patch and covering.

3. Summary of Experimental Results and Embodiments of the Invention

In summary, it has been discovered that lipid biosynthesis inhibitors such as HMG-CoA reductase inhibitors can be used to delay resealing of micropores prolonging pore viability and sustain drug delivery across MN-treated skin. More specifically, fluvastatin is a micropore lifetime enhancer for sustained delivery across MN-treated skin. The following is a summary of results of experiments described in the Examples of this application.

In vitro diffusion studies indicated that there was no significant difference in flux across MN-treated skin among the different treatment groups;

Skin concentration data indicated that there was no significant difference in the concentration of the µ-opioid antagonist, NTX, or the HGM-CoA reductase inhibitor, FLU in the skin irrespective of the method of FLU deposition;

Ethanol is preferable as the vehicle for FLU deposition;

Detectable levels of NTX were present in the plasma for 72 hours for all in vivo study groups; Recovery/healing of skin upon removal of occlusion following 7-day treatment with FLU in vivo occurred at 45 minutes;

Irritation studies show that there were no significant differences in skin irritation among the treatment groups immediately following treatment or at 5 minutes and 20 minutes post-removal of the patches at 7 days following treatment;

Staining studies indicate that pores were present in the FLU-treated group at the end of the 7-day patch application period compared with the absence of pores in the ethanol-treated vehicle control group.

4. Embodiments of the Invention

MN Arrays

The pharmaceutical compositions described herein are suitable for use in conjunction with MNs for transdermal drug delivery which create micrometer-scale transport pathways. MNs provide a minimally invasive means to transport molecules into and/or through the skin for local or systemic delivery of an active pharmaceutical agent. The channels or pores created by a MN array are extremely small on a clinical level. However, because the channels or pores are orders of magnitude larger than even macromolecules, such channels or pores have been shown to significantly increase skin permeability.

MNs can be can be solid or hollow and are made from many bio-compatible materials, including silicon, biodegradable polymers, and stainless steel. Solid MNs can be used to create channels or pores in the skin, followed by application of a transdermal patch to the skin surface. In an alternative embodiment, solid MNs can be first coated with an active pharmaceutical agent and then inserted into the skin. Hollow MNs can also be used to facilitate active permeation through the bore in the MN and into the skin. See, e.g., Prausnitz, MNs for transdermal drug delivery, Adv. 56 Drug. Deliv. Rev. 581-587 (2004), for a review of some of the MN technology suitable for use with the various embodiments of the claimed invention described herein.

Numerous studies have demonstrated that solid MNs can increase skin permeability by up to four orders of magnitude for compounds ranging in size from small molecules to proteins to nanoparticles. Henry et al., Microfabricated MNs: a novel approach to transdermal drug delivery, 87 J. Pharm. Sci. 922-925 (1998); McAllister et al., Microfabricated needles for transdermal delivery of macromolecules and nanoparticles: fabrication methods and transport studies, 100 Proc. Nat'l Acad. Sci. 13755-13760 (2003); Lin et al., Transdermal delivery of antisense oligonucleotides with microprojection patch (Macroflux) technology, 18(12) Pharm. Res. 1787-1793 (2001); and Cormier et al., Transdermal delivery of desmopressin using a coated MN array patch system, 97 J. Control. Release. 503-511 (2004). Hollow MNs have also been shown to deliver macromolecules such as insulin. See McAllister, Proc. Nat'l Acad. Sci. 13755-13760; Martanto et al., Transdermal delivery of insulin using MNs in vivo, 21 Pharm. Res. 947-952 (2004). MN insertion in human volunteers resulted in a sensation described as that similar to a smooth surface applied to the skin or the "sensation of a piece of tape" applied to the skin. Kaushik et al., Lack of pain associated with microfabricated MNs, 92 Anesth. & Analg. 502-504 (2001).

Suitable MN arrangements for use with the compounds and compositions described herein can be found in the foregoing references as well as in U.S. patent application Ser. No. 11/812,249, published as US 2008-0008745 A1 on Jan. 10, 2008.

In one embodiment, solid MN adhesive patches can be fabricated for insertion into the skin. In another embodiment, fixed MN geometries can be cut into 75 μm thick stainless steel sheets (Trinity Brand Industries, SS 304; McMaster-Carr, Atlanta, Ga., USA) using an infrared laser (Resonetics Maestro, Nashua, N.H., USA) and then can be manually bent perpendicular to the plane of their metal substrate. For better insertion and adhesion of patches to the skin, MN arrays can be assembled into adhesive patches. The adhesive would serve to hold the MNs firmly against the skin by compensating for the mechanical mismatch between the flexible skin tissue and the rigid MN substrate. The MN patches can be assembled in a laminar flow hood for cleanliness and then sterilized using ethylene oxide (AN 74j, Andersen Sterilizers, Haw River, N.C., USA) before use. The MN arrays can be fabricated to produce patches containing 50 MNs arranged in 5×10 arrays of MNs (FIG. 7A).

Each MN measured 620 μm in length, 160 μm in width at the base, and <1 μm in radius of curvature at the tip. To validate that these MNs pierced into the skin to increase skin permeability, individual arrays were inserted into the forearms of 10 human subjects. After removing the MN patches, the skin was stained with a dye that selectively stains sites of skin barrier perforation. As shown in FIG. 7B, all 50 MNs on the patch inserted into the skin and pierced the skin's SC barrier, as indicated by the 5×10 array of dyed spots corresponding exactly to the geometry of the MN array.

Lipid Biosynthesis Inhibitors

The term "lipid biosynthesis inhibitor" as used herein, refers to a compound employed to prevent the synthesis of the essential lipids required for lamellar body synthesis and thus the proper formation of the stratum corneum. Local concentrations of specific inhibitors of the three lipid synthesis pathways—namely cholesterol, fatty acids and ceramides—can be used to alter the molar ratio and delay barrier recovery. Examples of some of the inhibitors in certain embodiments include, but are not limited to, 5-(tetradecycloxy)-2-furancarboxylic acid (TOFA) for fatty acid synthesis, HMG-CoA reductase inhibitors i.e., fluvastatin (FLU), for cholesterol synthesis, and β-chloralanine (BCA) for ceramide synthesis.

Pharmaceutically acceptable forms of a lipid biosynthesis inhibitor include those which are suitable for transdermal administration to a mammal. The HMG-CoA reductase inhibitors described herein may be in any form suitable for administration to a mammal, such as in the form of a free base, free acid, salt, ester, hydrate, anhydrate, enantiomer, isomer, tautomer, polymorph, derivative, or the like.

Pharmaceutically acceptable salts of a lipid biosynthesis inhibitor include salts suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, beta-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of a lipid biosynthesis inhibitor may be prepared.

In one embodiment, acid addition salts can be prepared from the free base forms through a reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as person of ordinary skill in the art would appreciate that other acids may be used to create pharmaceutically acceptable salts of a lipid biosynthesis inhibitor. In other embodiments, an acid addition salt is reconverted to the free base by treatment with a suitable base. In still other embodiments, the basic salts are alkali metal salts, e.g., sodium salt.

Pharmaceutical Compositions and their Administration

In an embodiment, the active pharmaceutical agent within a pharmaceutical composition comprising a lipid biosynthesis inhibitor is administered to achieve a systemic therapeutic result. The pharmaceutical compositions and drug delivery systems described herein are suitable for the transdermal administration of an active pharmaceutical agent. In a further embodiment, the pharmaceutical compositions and drug delivery systems described herein are suitable for transdermal administration of an active pharmaceutical agent in order to achieve a systemic therapeutic benefit. In an additional embodiment, the pharmaceutical compositions and drug delivery systems described herein are suitable for topical administration of an active pharmaceutical agent. By way of example, and without limitation to the invention described herein, topical administration, can include, but is not limited to, administration to the epidermal and dermal regions of the skin. In a further embodiment, the pharmaceutical compositions and drug delivery systems described herein are suitable for administration of an active pharmaceutical agent in order to achieve a localized therapeutic benefit. By way of example, and without limitation to the invention described herein, topical therapeutic effects, can include, but are not limited to, therapeutic effects in the subcutaneous, muscular and joint regions near the area of administration. In another embodiment, the compositions and systems described herein are adapted for use in or on the abdomen, back, chest, legs, arms, scalp or other suitable skin surface and may be formulated as MN-containing patches to be used in conjunction with a MN array or other forms suitable for use in conjunction with a MN array such as ointments, creams, suspensions, lotions, pastes, gels, sprays, foams or oils which can be optionally occluded.

Certain embodiments are directed to pharmaceutical compositions that contain one or more lipid biosynthesis inhibitors such as HMG-CoA reductase inhibitors or derivatives thereof, preferably FLU, and an active pharmaceutical agent that is transdermally delivered, preferably an μ-opioid receptor antagonist, more preferably NTX, for sustaining delivery of a drug across MN-treated skin. Sustained delivery of the pharmaceutical composition will allow for treatment of a disease such as the reduction or treatment of opioid and alcohol addiction. These pharmaceutical compositions and kits comprising them may be formulated as described below and are typically in topical formulations including creams, ointments, lotions, and gels, preferably in an ointment that is topically applied for transdermal administration and is hydrophobic enough to keep the FLU and NTX in the ointment but also hydrophilic enough that it would not dry the skin and would be tolerated daily. Preferably, the contemplated pharmaceutical compositions include the inhibitory agents and active agents described herein in an amount sufficient to enhance lifetime of micropores in the skin to ultimately treat or reduce a disease such as opioid and alcohol addiction. The doses of active pharmaceutical agents for formulations to treat the diseases are discussed below.

Form of and Delivery of Pharmaceutical Formulations

The pharmaceutical compositions comprising the lipid biosynthesis inhibitor and active pharmaceutical agent to be transdermally delivered may exist in a wide variety of presentation forms, for example: in the form of liquid preparations as emulsions known in the art, or microemulsions, gels, oils, films, milks or lotions, lacquers, or foams.

Topical formulations are preferred. Delivery may occur via dropper or applicator stick, preferably via an intradermal or transdermal patch, or by simply spreading a formulation of the invention onto the affected area with fingers.

Pharmaceutical compositions may also include one or more emollients. An emollient is an oleaginous or oily substance, which helps to smooth and soften the skin, and may also reduce its roughness, flaking, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. In some embodiments, the emollient is a cocoglyceride, which is a mixture of mono-, di- and triglycerides of cocoa oil, sold under the trade name of Myritol 331 from Henkel KGaA, or Dicaprylyl Ether available under the trade name Cetiol OE from Henkel KGaA, or a $C_{12}$-$C_{15}$ Alkyl Benzoate sold under the trade name Finsolv$^{TN}$ from Finetex. Another suitable emollient is DC 200 Fluid 350, a silicone fluid.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Still other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the present invention ranging in amounts from about 1 percent to about 10 percent by weight, preferably about 5 percent by weight.

Certain embodiments may be in the form of a topical formulations that include an emulsion. These topical formulations can be in the form of the following:

Film

Ointment—Combines oil (80%) and water (20%). Effective barrier against moisture loss.

Gel—Liquefies upon contact with the skin.

Topical carriers for use in embodiments of the invention are disclosed in Remington: The Science and Practice of Pharmacy, 19th ed. (Alfonso R. Gennaro ed., 1995): 282-291. Suitable gels for use in the invention are disclosed in Remington: The Science and Practice of Pharmacy, 19th ed. (Alfonso R. Gennaro ed., 1995), 1517-1518; U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002. Dow Corning Corp. As used herein, a pharmaceutically acceptable topical carrier is any pharmaceutically acceptable formulation that can be applied to the skin surface for topical, dermal, intradermal, or transdermal delivery of a pharmaceutical or medicament. Pharmaceutical formulations of the invention are typically prepared by mixing a HMG-CoA reductase inhibitor (e.g., FLU or derivatives thereof) with a drug, such as a μ-opioid antagonist (e.g., NXT or derivatives thereof) and a topical carrier, according to well-known methods in the art. The topical carriers include pharmaceutically acceptable solvents, such as a polyalcohol or water; emulsions (either oil-in-water or water-in-oil emulsions), such as creams or lotions; micro emulsions; gels; and ointments. Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Topical pharmaceutical formulations of the invention in the form of an emulsion may optionally contain drying agents. Drying agents generally promote rapid drying of moist areas and coats the skin for protection and healing. In particular, it acts to prevent irritation of the involved area and water loss from the skin layer by forming a physical barrier on the skin. Preferred drying agents include calamine, copper sulfate, kaolin, potassium permanganate, Burow's aluminum solution, talc, starches such as wheat and corn starch, silver nitrate, acetic acid, and zinc-containing drying agents such as zinc oxide, zinc acetate, zinc stearate, and zinc sulfate.

Or these pharmaceutical formulations may be in the form of an aqueous solution or suspension, preferably, an aqueous solution. Suitable aqueous topical formulations for use in the invention are disclosed in Remington: The Science and Practice of Pharmacy, 19th ed. (Alfonso R. Gennaro ed., 1995), 1563-1576. Other suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002.)

The pharmaceutical compositions and drug delivery systems described herein can, if desired, include one or more pharmaceutically acceptable excipients. The term "excipient" herein means any substance, not itself an active pharmaceutical agent, used in conjunction with the active pharmaceutical agent delivered to a subject or added to a pharmaceutical composition or drug delivery system to improve one of more characteristics, such as its handling or storage properties or to permit or facilitate formation of a dose unit of the composition. Excipients include, by way of illustration and not limitation, solvents, thickening agents, penetration enhancers, wetting agents, lubricants, emollients, substances added to mask or counteract a disagreeable odor or flavor, fragrances, and substances added to improve appearance or texture of the composition or drug delivery system. Any such excipients can be used in any dosage forms of the present disclosure. The foregoing list of excipients is not meant to be exhaustive but merely illustrative as a person of ordinary skill in the art would recognize that additional excipients could be utilized.

The pharmaceutical compositions and transdermal drug delivery systems described herein containing excipients can be prepared by any technique known to a person of ordinary skill in the art of pharmacy, pharmaceutics, drug delivery, pharmacokinetics, medicine or other related discipline that comprises admixing one or more excipients with a therapeutic agent to form a composition, drug delivery system or component thereof.

The pharmaceutical compositions can comprise pharmaceutically acceptable excipients other than emollients, demulcents, and antioxidants such as those listed in Remington: The Science and Practice of Pharmacy, 19th ed. (Alfonso R. Gennaro ed., 1995), 866-885. According to Transdermal and Topical Drug Delivery Systems (Ghosh, T. K. et al., eds., 1997), these include, but are not limited to, protectives, adsorbents, preservatives, moisturizers, buffering agents, solubilizing agents, skin-penetration agents, and surfactants.

Suitable demulcents include, but are not limited to, benzoin, hydroxypropyl cellulose, hydroxypropyl methylcellulose, and polyvinyl alcohol. Suitable emollients include, but are not limited to, animal and vegetable fats and oils, myristyl alcohol, alum, and aluminum acetate. Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates. More specifically, camphor is slightly soluble in water, soluble in alcohol, ether, benzene, acetone, oil of turpentine, glacial acetic acid, chloroform, carbon disulphide, solvent naphtha and fixed and volatile oils. It is also soluble in aniline, nitrobenzene, tetralin, decalin, methylhexalin, petroleum ether, higher alcohols, concentrated mineral acids, phenol, liquid ammonia and liquid sulphur dioxide.

Embodiments may include further skin-penetration agents such as, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methyl pyrrolidone.

In treating in the preferred form of a transdermal patch, the pharmaceutical formulation is contained within a laminated structure that serves as a drug delivery device to be affixed to the skin. In such a structure, the pharmaceutical formulation is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients—containing composition. Alternatively, the active ingredients—containing reservoir and skin contact adhesive are present as separate and distinct layers, with the adhesive underlying the reservoir which, in this case, may be either a polymeric matrix as described above, or it may be a liquid or hydrogel reservoir, or may take some other form.

In an embodiment, the inhibitory agents and active agents are formulated into liposomes for delivery. Liposomes are microscopic spheres made from fatty materials, predominantly phospholipids. Because of their similarity to phospholipid domains of cell membranes and an ability to carry substances, liposomes can be used to protect active ingredients and to provide time-release properties in medical treatment. Liposomes are made of molecules with hydrophilic and hydrophobic ends that form hollow spheres. They can encapsulate water-soluble ingredients in their inner water space, and oil-soluble ingredients in their phospholipid membranes. Liposomes are made up of one or more concentric lipid bilayers, and range in size from 50 nanometers to several micrometers in diameter. Liposomal formulations have been used for many years to enhance the penetration of topically applied ingredients. Liposomes are made from lecithin, egg or it can be synthesized. These phospholipids can be both hydrogenated and non-hydrogenated. Phosphatidylcholine is extracted from these sources and can be both saturated and unsaturated. Other phospholipids including essential fats like linoleic acid and alpha linolenic acid can be used. Additionally, polyethylene glycol and cholesterol are considered liposomal material because of their lipid structure.

The active pharmaceutical agents that can be transdermally administered using the methods described herein are not limited. Indeed, traditional limitations or constraints placed upon the transdermal administration of an active pharmaceutical agent such as the molecular weight or size, molecular charge or water/octanol partition coefficients are not limiting factors when the active pharmaceutical agent is administered with MNs and a lipid biosynthesis inhibitor as described herein. Indeed, very large molecules such as proteins, antibodies, peptides, DNA, vaccines and nanoparticles, which would otherwise typically be considered unsuitable for other transdermal passive diffusion systems, can be delivered through the skin for local and/or systemic action. Additionally, active pharmaceutical agents which are water soluble have traditionally been thought to be unsuitable for transdermal delivery due to the lipid nature of the stratum corneum. However, with the use of the MN and lipid biosynthesis inhibitor as described herein, even highly water soluble compounds can be transdermally delivered via the pores created by MN treatment of the skin. Thus, nearly any type or class of active pharmaceutical agent can be delivered in conjunction with a MN treatment of the skin and use of a lipid biosynthesis inhibitor as described herein.

Dosages and Dosing Frequency

In the experiments herein, FLU and NTX were tested. It is believed that frequent reapplication or formulation issues would not arise with FLU treatment, since only very small concentrations were required for previously published studies. FLU is a well-known statin drug and the dosage, metabolism, pharmacokinetics and toxicity profile are well established in humans See MICROMEDIX® 1.0 (Healthcare Series) and https://scifinder.cas.org/ Copyright © 2012 American Chemical Society. The lowest therapeutically relevant oral daily dose is 20 mg and the oral bioavailability is 9-50%. See MICROMEDIX® 1.0 (Healthcare Series). Even if the bioavailability is 100% from the topical formulation, the maximum delivered dose would be 1.2 mg over 7 days, which is significantly below the therapeutic dose. For naltrexone, the currently approved dosage forms include oral and an extended release intramuscular injection See MICROMEDIX® 1.0 (Healthcare Series) and Alkermes Vivitrol (naltrexone for extended release injectable suspension; http://www.vivitrol.com/). The oral dosage form has issues with variable bioavailability and compliance in its treatment population due to daily dosing and side effects See MICROMEDIX® 1.0 (Healthcare Series) and Vivitrol (Naltrexone XR inj) 2013. The extended release intramuscular injection is difficult to remove if there is a need for emergency opiate treatment, and also leads to injection site reactions (See Alkermes Vivitrol (naltrexone for extended release injectable suspension; http://www.vivitrol.com/ and Porter S J, et al. 2000. Kinetics and inhibition of the formation of 6-naltrexol from naltrexone in human liver cytosol. Br J Clin Pharmacol 50: 465-471.) It has been previously shown that by using MN, NTX can be delivered at therapeutic levels for 2-3 days in humans. See Wermeling D P et al. 2008. MNs permit transdermal delivery of a skin-impermeant medication to humans. Proceedings of the National Academy of Sciences 105: 2058-2063.

In certain embodiments, a single dosage unit comprises a lipid biosynthesis inhibitor and a therapeutically effective amount or a therapeutically and/or prophylactically effective amount of an active pharmaceutical agent. The term "therapeutically effective amount" or "therapeutically and/or prophylactically effective amount" as used herein refers to an amount of active pharmaceutical agent that is sufficient to elicit the required or desired therapeutic and/or prophylactic response, as the particular treatment context may require. Single dosage unit as used herein includes individual patches which incorporate at least a lipid biosynthesis inhibitor which can be applied after the skin has been treated with a MN array which forms pores through which an active pharmaceutical agent can be delivered.

It will be understood that a therapeutically and/or prophylactically effective amount of a drug for a subject is dependent, inter alia, on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic, farm or companion animal, illustratively a cat, cow, pig, dog or a horse as well as laboratory animals such as guinea pigs and primates.

In another embodiment, pharmaceutical compositions disclosed herein comprise a first active pharmaceutical agent in a total amount of about of between about 0.1% and about 95% by weight of the composition which is transdermally administrable, for example about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

Dosages and dosing frequency will be determined by a trained medical professional depending on the activity of the HMG-CoA reductase inhibitor or of an active pharmaceutical agent such as a µ-opioid antagonist or derivatives thereof, the dose, the particular topical formulation, and the identity and severity of the dermatologic disorder. As described above, therapeutically effective amounts of FLU range 0.1 to 10 mg/cm$^2$, preferably 0.6 mg/cm$^2$, and therapeutically effective amounts of NTX range from about 10 to 100 mg/cm$^2$, preferably 27 mg/cm$^2$.

Transdermal Drug Delivery Systems

As used herein, a "transdermal drug delivery system" comprises an array of MNs used in conjunction with lipid biosynthesis inhibitor such as a HMG-CoA reductase inhibitor, preferably FLU. Various alternative embodiments described and claimed herein include (i) the use of a lipid biosynthesis inhibitor-containing gel that could be applied to the skin surface either before, during, or after the skin had been treated with a MN array such as a MN array device; (ii) a patch comprising a lipid biosynthesis inhibitor and an active pharmaceutical agent could be applied to the skin surface after the skin had been treated with a MN array such as a MN array device (iii) an patch application could be incorporated with a MN array application device; (iv) the lipid biosynthesis inhibitor could be part of a MN coating; and (v) lipid biosynthesis inhibitor could be part of a formulation which is delivered through hollow MNs and into the skin.

In one embodiment, the pharmaceutical compositions described herein are suitable for use in transdermal delivery systems such as a patch to be used in conjunction with a MN array. The pharmaceutical compositions described herein are suitable for use in a membrane-modulated transdermal delivery system. In one embodiment, the reservoir containing the active pharmaceutical agent to be transdermally administered to the patient can be encapsulated in a shallow compartment molded from a drug impermeable backing and a rate controlling polymeric membrane through which the compound to be delivered passes in a controlled manner. In another embodiment, the external surface of the membrane has a thin layer of a drug-compatible, hypoallergenic adhesive polymer (e.g., silicone or polyacrylate adhesive) which is applied to achieve intimate contact of the transdermal system with the skin.

Also, the pharmaceutical compositions described herein are suitable for use in adhesive-diffusion controlled transdermal systems in conjunction with a MN array. In these embodiments, the drug reservoir can be formulated by directly dispersing the active pharmaceutical agent (or agents) to be delivered in an adhesive polymer and then spreading the medicated adhesive onto a flat sheet of drug-impermeable backing membrane to form a thin active pharmaceutical agent reservoir layer. Optionally, on top of the drug reservoir layer, additional layers of non-medicated rate controlling adhesive polymer of constant thickness are placed to produce an adhesive diffusion-controlled drug-delivery system. The resulting adhesive-diffusion controlled transdermal system is then applied to the area of the skin which has previously undergone MN treatment.

The pharmaceutical compositions described herein are also suitable for use in matrix dispersion-type systems in conjunction with MN arrays. In these systems, the reservoir containing the active pharmaceutical agent (or agents) can be formed by homogeneously dispersing the active pharmaceutical agent (or agents) in a hydrophilic or lipophilic polymer matrix, and the medicated polymer then is molded into a medicated disc with a defined surface area and controlled thickness. The disc then is glued onto an occlusive baseplate in a compartment fabricated from a drug-impermeable backing. The adhesive polymer is spread along the circumference to form a strip of adhesive rim around the medicated disc. The resulting dispersion-type transdermal system is then applied to the area of the skin which has previously undergone MN treatment.

The pharmaceutical compositions described herein are also suitable for use in microreservoir systems in conjunction with MN arrays. In these systems, the drug reservoir is formed by first suspending the drug particles in an aqueous solution of water-soluble polymer and then dispersing it homogeneously in a lipophilic polymer by high-shear mechanical force to form a large number of unleachable, microscopic spheres reservoirs of active pharmaceutical agent (or agents). This unstable dispersion is quickly stabilized by immediately cross-linking the polymer which produces a medicated polymer disc with a constant surface area and fixed thickness. A transdermal therapeutic system is produced in which the medicated disc is positioned at the center and surrounded by an adhesive rim. The resulting microreservoir transdermal system is then applied to the area of the skin which has previously undergone MN treatment.

In one embodiment, the drug and adhesive are formulated into one monolithic layer. The drug can be mixed with an adhesive (e.g. silicone type, available from Dow Corning and other manufacturers) in a solvent (e.g. methylene chloride or ethyl acetate). This drug mixture would then be extruded onto a polyester backing film to a uniform thickness of about 100 microns or greater with a precision wet-film applicator. The solvent is allowed to evaporate in a drying oven and the resulting "patch" is trimmed to the appropriate size. Various patch formulations will be made until the desired steady-state flux rate and adhesive properties are obtained. Different adhesives can be tried, as well as varying the amount of adhesive in the formulation (Nalluri, Milligan et al. 2005). Suitable results have been obtained by making monolithic patches with DURO-TAK 387-2051, which is an acrylate-vinyl acetate non-curing pressure sensitive adhesive from the National Starch Chemical Company. Different solvents (e.g. isopropyl myristate, propylene glycol) can optionally be incorporated into the formulation in an attempt to optimize the delivery rate of the active pharmaceutical agent. In a further embodiment, reservoir patches can be made if it appears, for example, that the drugs are not compatible with a monolithic matrix patch formulation. In the reservoir system, the active ingredient(s) and any excipient(s) could be formulated into a gel and sealed between a release layer and an impermeable backing material such as polyester or other suitable material known to a person of skill in the art. Ethyl vinyl acetate membranes with acrylic adhesives have been found to be suitable. In each of the foregoing embodiments, the patch would then be applied to the area of the skin which has previously undergone MN treatment.

Adhesive patch formulations can be prepared containing different loadings of the active pharmaceutical agent (or agents) to be delivered transdermally by using DURO-TAK adhesives (National Starch and Chemical Company, USA). Appropriate amounts of adhesive and drug can be sonicated for ten minutes, cast onto the release liner (9742 Scotchpak, 3M, St. Paul, Minn.) with a wet film applicator (Paul N. Gardner Company, Inc., Pompano Beach, Fla.) set at a 40 mil thickness, and kept at room temperature for one hour and then at 70.degree. C. in an oven for ten minutes (to remove any residual solvent). The patches would then be covered with backing membrane (CoTran 9722, 3M, St. Paul, Minn.), will be cut into appropriate sizes, and then can be stored in a desiccator for further study. The resulting patches would then be applied to the area of the skin which has previously undergone MN treatment.

In further embodiments, additional adhesives which are suitable for preparing patch formulations and transdermal delivery systems such as patches include polyisobutylenes, acrylates, silicone and combinations of the foregoing. Additional adhesives can be found in U.S. patent application Ser. No. 11/860,432, published as US 2008/0076789 on Mar. 27, 2008.

The pharmaceutical compositions described herein are also suitable for use the use of a lipid biosynthesis-containing gel that could be applied to the skin surface either before, during or after the skin had been treated with a MN array. In a further embodiment, in addition to the lipid biosynthesis inhibitor, the gel would also contain an active pharmaceutical agent.

In another embodiment, the transdermal patch incorporating a lipid biosynthesis inhibitor and an active pharmaceutical agent is applied to the area of the skin which has undergone MN treatment and is capable of controlling the release of the active pharmaceutical agent such that transdermal delivery of the active pharmaceutical agent to the subject is substantially uniform and sustained over a period of about 1 hour, about 2 hours, about 3 hours, about 4 hours, about 6 hours, about 12 hours, about 24 hours, about 48 hours, about 72 hours, about 96 hours, about 5 days, about 6 days or about 7 days. Such transdermal patches which can be used in the practice of the methods described herein can take the form of an occlusive body. In practice, the occlusive body which includes the lipid biosynthesis inhibitor and an active pharmaceutical agent is applied to the area of the skin which has undergone MN treatment to transdermally deliver the active pharmaceutical agent.

In certain embodiments, these transdermal drug delivery systems may include an array of MNs as described above, and a coating disposed on the MNs, wherein the coating comprises a HMG-CoA reductase inhibitor selected from the group consisting of atorvastatin, fluvastatin, pitavastatin, pravastatin, rosuvastatin, and simvastatin. As used herein, the HMG-CoA reductase inhibitor may be a pharmaceutically acceptable salt thereof, and/or a combination of free base and pharmaceutically acceptable salt. The HMG-CoA reductase inhibitor weight may be established by well-known methods in the art.

The present coating may also include at least one excipient to form a coating formulation. An excipient can function to maintain the active nature of the HMG-CoA reductase inhibitor, to facilitate the performance of a coating formulation when depositing a coating on the MNs, to resist disruption of the coating when penetrating the stratum corneum. Accordingly, for some embodiments that include a coating deposited on the MN itself comprising the HMG-CoA reductase inhibitor, the coating or MN itself further comprises at least one excipient.

The amount of the at least one excipient in the coating or coating formulation may vary depending on the identity of the components in the coating formulation, the amount of HMG-CoA reductase inhibitor desired on the MN array, the type of MN array being coated, the shape and location of the coating on the MN, other considerations not discussed herein, or some combination thereof.

Exemplary excipients can include, for example buffers, carbohydrates, polymers, amino acids, peptides, surfactants, proteins, non-volatile nonaqueous solvents, acids, bases, antioxidants, and saccharin.

At least one buffer may be used for at least a portion of the at least one excipient. The buffer can generally function to stabilize the pH of a coating formulation used for depositing the coating on the MNs. The particular buffer to be utilized can depend at least in part on the HMG-CoA reductase inhibitors that are included in the coating. The pH of the formulation can, for example, help to maintain the solubility of HMG-CoA reductase inhibitors at a desired level. Generally, commonly utilized buffers can be used in the coating formulations.

Exemplary buffers can include for example, histidine, phosphate buffers, acetate buffers, citrate buffers, glycine buffers, ammonium acetate buffers, succinate buffers, pyrophosphate buffers, Tris acetate (TA) buffers, and Tris buffers. Buffered saline solutions can also be utilized as buffers. Exemplary buffered saline solutions include, for example, phosphate buffered saline (PBS), Tris buffered saline (TBS), saline-sodium acetate buffer (SSA), saline-sodium citrate buffer (SSC).

At least one carbohydrate, including mixtures of carbohydrates, may be used for at least a portion of the at least one excipient. The carbohydrate can be a saccharide, including mono-, di-, and polysaccharides, and may include, for example, non-reducing sugars such as raffinose, stachyose, sucrose, and trehalose; and reducing sugars such as monosaccharides and disaccharides. Exemplary monosaccharides can include apiose, arabinose, digitoxose, fucose, fructose, galactose, glucose, gulose, hamamelose, idose, lyxose, mannose, ribose, tagatose, sorbitol, xylitol, and xylose. Exemplary disaccharides can include for example sucrose, trehalose, cellobiose, gentiobiose, lactose, lactulose, maltose, melibiose, primeverose, rutinose, scillabiose, sophorose, turanose, and vicianose. In embodiments, sucrose, trehalose, fructose, maltose, or combinations thereof can be utilized. All optical isomers of exemplified sugars (D, L, and racemic mixtures) are also included herein.

Polysaccharides can include for example starches such as hydroxyethyl starch, pregelatinized corn starch, pentastarch, dextrin, dextran or dextran sulfate, gamma-cyclodextrin, alpha-cyclodextrin, beta-cyclodextrin, glucosyl-alpha-cyclodextrin, maltosyl-alpha-cyclodextrin, glucosyl-beta-cyclodextrin, maltosyl-beta-cyclodextrin, 2-hydroxy-beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, and sulfobutylether-gamma-cyclodextrin. In embodiments, hydroxyethyl starch, dextrin, dextran, gamma-cyclodextrin, beta-cyclodextrin, or combinations thereof can be utilized. In embodiments, dextrans having an average molecular mass of 35,000 to 76,000 can be utilized.

The at least one carbohydrate can be a cellulose. Suitable celluloses can include for example hydroxyethyl cellulose (HEC), methyl cellulose (MC), microcrystalline cellulose, hydroxypropyl methyl cellulose (HPMC), hydroxyethylmethyl cellulose (HEMC), hydroxypropyl cellulose (HPC), and mixtures thereof.

At least one polymer may be used for at least a portion of the at least one excipient. Suitable polymers include, for example, polyvinyl pyrrolidone (PVP), polyethylene glycol (PEG), polyvinyl alcohol (PVA), and polyethylene glycol sorbitan isostearate. In embodiments, polyvinyl pyrrolidones (PVP) having an average molecular weight of 10,000 can be utilized. In embodiments, polyvinyl pyrrolidones (PVP) having an average molecular weight of 5,000 to 1.5 million can be utilized. In embodiments, polyethylene glycols having an average molecular weight of 300 to 8,000 can be utilized.

At least one amino acid may be used for at least a portion of the at least one excipient. Suitable amino acids can include for example lysine, histidine, cysteine, glutamate, lysine acetate, sarcosine, proline, threonine, asparagine, aspartic acid, glutamic acid, glutamine, isoleucine, leucine, methionine, phenylalanine, serum tryptophan, tyrosine, valine, alanine, arginine, and glycine. In many cases the salt form of the amino acids can be used to increase the aqueous solubility of the amino acid in an aqueous media or formulation.

At least one peptide may be used for at least a portion of the at least one excipient. The amino acids making up the peptide may be the same or at least some may be different from each other. Suitable polyamino acids (the same amino acids) can include for example polyhistidine, polyaspartic acid, and polylysine.

At least one protein may be used for at least a portion of the at least one excipient. Suitable proteins can include for example human serum albumin and bioengineered human albumin.

At least one saccharin may be used for at least a portion of the at least one excipient. In one example, the saccharin is saccharin sodium dihydrate.

At least one lipid may be used for at least a portion of the at least one excipient. In one example, the lipid may be dipalmitoylphosphatidylcholine (DPPC).

At least one acid and/or base may be used for at least a portion of the at least one excipient. For example, at least one weak acid, weak base, strong acid, strong base, or some combination thereof may be used. Acids and bases can serve the purpose of solubilizing or stabilizing the HMG-CoA reductase inhibitors. These acids and bases can be referred to as counterions. These acids and bases can be organic or inorganic. Exemplary weak acids include for example acetic acid, propionic acid, pentanoic acid, citric acid, succinic acid, glycolic acid, gluconic acid, glucuronic acid, lactic acid, malic acid, pyruvic acid, tartaric acid, tartronic acid, fumaric acid, glutamic acid, aspartic acid, malonic acid, butyric acid, crotonic acid, digylcolic acid, and glutaric acid. Exemplary strong acids include for example hydrochloric acid, hydrobromic acid, nitric acid, sulfonic acid, sulfuric acid, maleic acid, phosphoric acid, benzene sulfonic acid, and methane sulfonic acid. Exemplary weak bases include for example ammonia, morpholine, histidine, lysine, arginine, monoethanolamine, diethanolamine, triethanolamine, tromethamine, methylglucamine, and glucosamine. Exemplary strong bases include for example sodium hydroxide, potassium hydroxide, calcium hydroxide, and magnesium hydroxide.

At least one surfactant may be used for at least a portion of the at least one excipient. The at least one surfactant can be amphoteric, cationic, anionic, or nonionic. Suitable surfactants can include for example lecithin, polysorbates (such as polysorbate 20, polysorbate 40, and polysorbate 80 for example), glycerol, sodium lauroamphoacetate, sodium dodecyl sulfate, cetylpyridinium chloride (CPC), dodecyltrimethyl ammonium chloride (DoTAC), sodium desoxycholate, benzalkonium chloride, sorbitan laurate, and alkoxylated alcohols (such as laureth-4).

At least one inorganic salt may be used for at least a portion of the at least one excipient. Suitable inorganic salts can include for example sodium chloride, and potassium chloride.

A non-volatile, non-aqueous solvent may also be used for at least a portion of the at least one excipient. Examples may include propylene glycol, dimethylsulfoxide, glycerin, 1-methyl-2-pyrrolidinone, N,N-dimethylformamide, and the like.

At least one antioxidant may be used for at least a portion of the at least one excipient. Suitable antioxidants can include for example sodium citrate, citric acid, ascorbic acid, methionine, sodium ascorbate, and combinations thereof.

For certain embodiments, including any one of the above embodiments which includes an excipient, preferably the at least one excipient is selected from the group consisting of sucrose, dextrins, dextrans, hyroxyethyl cellulose (HEC), polyvinyl pyrrolidone (PVP), polyethylene glycols, amino acids, peptides, polysorbates, human serum albumin, saccharin sodium dihydrate, and a combination thereof.

For certain embodiments, including any one of the above embodiments which includes an excipient, the at least one excipient is a saccharide. For certain of these embodiments, the saccharide is selected from the group consisting of dextran, sucrose, trehalose, and a combination thereof.

As indicated above, the method of making a HMG-CoA reductase inhibitor-coated MN device is provided herein. The amounts of these ingredients in the coating formulation are chosen in order to achieve the above described amounts of the solid, non-volatile ingredients in the resulting coating deposited on the MNs. This coating formulation may further include any of the excipients as described above and amounts thereof in order to achieve the amounts in the deposited coating as described above. The coating is deposited on the MNs by contacting the MNs with the composition.

As indicated above, the method of making a HMG-CoA-reductase inhibitor-coated MN device provided herein includes a step of providing an array of MNs. The step of providing the MN array can be accomplished by manufacturing the MN array, obtaining a MN array (for example by purchasing the MN array), or by some combination thereof.

Generally, a MN array includes a plurality of MNs.

A MN or the plurality of MNs in a MN array can be characterized by shape. For certain embodiments, including any one of the embodiments described herein, each of the plurality of MNs can have a square pyramidal shape or the shape of a hypodermic needle. For certain of these embodiments, preferably the shape is square pyramidal.

For certain embodiments, including any one of the embodiments described herein, the device may be in the form of a patch. One example of such an embodiment comprises a patch in the form of a combination of a MN array, pressure-sensitive adhesive, and backing. The MNs may be arranged in any desired pattern or distributed over the MN substrate randomly. The MNs may be arranged in uniformly spaced rows.

In the method of making a local anesthetic-coated MN device described herein, the step of contacting the MNs with the HMG-CoA reductase inhibitor can be carried out by dip coating the MNs.

When the MNs are contacted with the coating formulation, the MNs are facing downward into the coating formulation. For certain embodiments, preferably after the MNs are contacted with the HMG-CoA reductase inhibitor, contacting is terminated and the MNs are positioned facing upward prior to and/or during volatilizing at least a portion of the volatilizable carrier. In this position, a portion of the HMG-CoA reductase inhibitor remaining on the MNs may flow toward the base, leaving the tips of the MNs exposed or with only a small amount of HMG Co-A reductase inhibitor on the tips. The degree to which flow occurs can depend upon factors such as the viscosity, contact angle, and surface tension as described above.

After removing the MNs, some of the coating formulation remains on the MNs, the amount depending upon the coating formulation properties and surface properties of the MN material as described above. At least a portion of the volatilizable carrier is removed from the coating formulation adhering to the MNs, leaving the coating disposed on the MNs. One or more additional contacting steps may be used. The shape of the coating, average coating thickness, and amount of the surface of the MN covered by the coating depends upon the factors discussed above as well as the number of times the contacting step is repeated.

Methods of coating MN arrays are well known in the art and numerous technologies can be used to form coated MN arrays. A coating disposed on the MNs or the coated MN array can include a coating on at least a portion of the plurality of MNs.

Method of Enhancing MN Pore Viability for Sustained Delivery of a Drug Across MN-Treated Skin Methods for enhancing MN pore viability are described herein and comprise the use of a MN array to create pores in the skin of a mammal and topically applying a lipid biosynthesis inhibitor in conjunction with the use of the MN array wherein the resulting pores have enhanced viability so that the rate and extent of transdermal delivery of an active pharmaceutical agent is increased relative to the non-use of a lipid biosynthesis inhibitor. In other embodiments the lipid biosynthesis inhibitor can be a HMG-CoA reductase inhibitor such as FLU. In a further embodiment the lipid biosynthesis inhibitor can be in any pharmaceutically acceptable form.

In some embodiments, methods are provided for enhancing MN pore viability and then ultimately sustaining delivery of a drug transdermally across MN-treated skin for a period of about 7 days. MN enhanced transdermal delivery has been established as a safe, effective and pain free method for drug delivery over the last decade. However, the resealing of the micropores is a rate limiting step in effective delivery of drugs across MN treated skin for more than 48 hours.

Pore lifetime enhancement methods have been explored in the literature to enhance the drug delivery window. One such method is topical application of Solaraze® (3% diclofenac sodium, 2.5% hyaluronic acid), a non-steroidal anti-inflammatory drug. The results from impedance spectroscopy, TEWL and pharmacokinetics (hereinafter "PK") studies in animal models and humans indicated that daily/alternate day application of diclofenac allowed drug delivery for a period of 7 days compared to 2-3 days in the absence of a pore lifetime enhancement agent in the formulation, following MN treatment. See Banks S. et al., 2011. Diclofenac Enables Prolonged Delivery of Naltrexone Through MN-Treated Skin. Pharm. Res.: 1-9; Brogden N K, et al., 2012. Diclofenac Delays Micropore Closure Following MN Treatment in Healthy Human Subjects. J of Controlled Release 163(2): 220-9; AND Brodgen N K. Clinical Evaluation of Novel Methods for Extending MN Pore Lifetime 2012. However, the studies required frequent application of diclofenac, which is not ideal for a 7-day transdermal patch system, and formulating high concentrations of diclofenac at the skin surface pH of around 5 was difficult due to the physicochemical properties of the molecule.

It has been discovered, and is disclosed in certain embodiments, that FLU, a lipid biosynthesis inhibitor and HMG-CoA reductase inhibitor, can be utilized as a pore lifetime enhancement agent. Cholesterol is required for the normal turnover process of the SC in addition to healing. Without being bound by theory, it might be possible that local application of the HMG-CoA reductase inhibitors decrease cholesterol synthesis in the entire treated region leading to malformation of the barrier.

Expression levels of mRNA of most enzymes of the lipid biosynthesis pathway are upregulated following insults to the SC barrier. See Tsai J, et al., 1996. Metabolic approaches to enhance transdermal drug delivery. 1. Effect of lipid synthesis inhibitors. J of Pharma Sciences 85: 643-648. Inhibitors of these enzymes have been shown to delay barrier recovery following acetone or surfactant treatment. See Li Y Z, et al., 2009. Trypsin as a novel potential absorption enhancer for improving the transdermal delivery of macromolecule. J Pham Pharmacol 61: 1005-1012. Since the exact nature of barrier insult following MN treatment is not well established, certain embodiments of the invention evaluate the effect of FLU as a one-time topical application on micropore healing and drug delivery using pharmacokinetics and TEWL for evaluation. Frequent reapplication or formulation issues should not arise with FLU treatment as compared to diclofenac, since only very small concentrations of potent lipid biosynthesis inhibitors were required for previously published studies. It is believed that down regulation of cholesterol synthesis leads to delay in barrier recovery and therefore enhances the drug delivery window.

The HMG-CoA reductase inhibitor, FLU, (M.W. 411.47, log P 4.6, pKa 4.27) as used in certain embodiments is a well-known statin drug and the dosage, metabolism, pharmacokinetics and toxicity profile is well established in humans. See MICROMEDEX® 1.0 (Healthcare Series) and https://scifinder.cas.org. The lowest therapeutically relevant oral daily dose is 20 mg and the oral bioavailability is 9-50%. See MICROMEDEX® 1.0 (Healthcare Series). Therefore, even if the bioavailability is 100% from the topical formulation, the maximum delivered dose would be 1.2 mg over 7 days, which is significantly below the therapeutic dose.

In order to optimize FLU skin concentration and NTX flux, in certain embodiments, four different methods were chosen for FLU deposition. The results indicated that there was no significant difference in NTX flux or skin concentration of FLU using any of the deposition methods. Ethanol (200 proof) was chosen for in vivo studies because it is a frequently used topical excipient and most of the 40 μl ethanol used was allowed to evaporate before application of the drug gel. Acetone is similar in action to ethanol; however it caused irritation in the MN-treated animal models (data not shown) and thus was not used for in vivo studies. The other two formulations tested contained either 70% or 25% PG. PG has been shown to interact with the underlying dermis and microchannels in MN treated skin. See Ghosh P. et al., 2013. Development of a codrug approach for sustained delivery across MN treated skin. J. Pharm Sci. The high viscosity of PG rich formulations significantly decreased flux across MN treated skin, as compared to an aqueous formulation. See Milewski M., Stinchcomb A 2011. Vehicle Composition Influence on the MN-Enhanced Transdermal Flux of Naltrexone Hydrochloride. Pharmaceutical Research 28: 124-134. The formulations also contained large amounts of ethanol, a known permeation enhancer, and evaporation of the ethanol from these was not as efficient due to the presence of PG. Solubility of FLU was not an issue with any of the formulations. Therefore, in a preferred embodiment, 40 μl of 1.5% FLU in 200 proof ethanol was chosen as the vehicle for FLU deposition. Ethanol is a well-known chemical enhancer used in the topical/transdermal industry. It acts by replacing the water molecules in the lipid polar head groups as well as the protein regions of the SC, thus enhancing free volume and permeability of molecules across the skin. See Feingold K R 2009. The outer frontier: the importance of lipid metabolism in the skin. J Lipid Res 50 Suppl: 5417-22. Therefore, a control was used in PK, recovery and irritation studies to evaluate the effect of ethanol alone on micropore lifetime.

PK studies were used in certain embodiments (Example 3) as they are the most direct measure of drug delivery and micropore closure. In certain embodiments, three different groups were evaluated to look at the effect of FLU in ethanol and MN, ethanol only and MN, and MN only in HGP. A non-MN treated control was not evaluated for animal studies since it is known that permeation of ionized species like NTX HCL is limited across the intact SC. The PK data indicated that for the MN only control, plasma concentration dropped below 2 ng/ml beyond 58 h. These data are in agreement with previously published pharmacokinetic data where the drug delivery window following one time application of MN was shown to be between 48-72 hours. See Wermeling D P et al. 2008, and Banks S, et al. 2011. The treatment group showed NTX levels above 2 ng/ml for the entire length of the study, as compared to the vehicle control group which showed levels above 2 ng/ml until 144 hours. The AUC values for the treatment group and the vehicle control group were not significantly different from each other indicating that ethanol treatment alone also enhanced the drug delivery following MN treatment. The $C_{max}$ and $T_{max}$ values indicated that treatment of all animals was consistent across the treatment groups. Drug was quantified in plasma within 15 minutes of treatment indicating that there is no significant lag time associated with the patch system. Such profiles are commonly observed for MN treatment and immediate delivery in addition to sustained release is one of the advantages of such a delivery system. The shape of the plasma concentration time curve is consistent with reported profiles of MN enhanced delivery, where a peak is observed immediately following patch application followed by a decline in the plasma concentration due to resealing of the micropores. Such data can be modeled using a 3 compartment model for drug permeation across skin, pharmacokinetics of the drug in the body, and healing of the micropores. See Ghosh P. et al., 2013. Rate of micropore resealing in the presence of an active pore lifetime enhancement agent can then be estimated if permeation values are known from in vitro studies and PK estimates are obtained from in vivo studies. Thus from the PK studies it can be concluded that both FLU and an ethanol vehicle can be used to enhance the drug delivery window; however, the exact mechanism of ethanol action is not known.

Recovery of the skin, i.e, regeneration of barrier function and irritation of skin following local application of biochemical inhibitors and permeation enhancers are important aspects during development of transdermal delivery systems for chemical enhancement techniques. See Thong H Y, et al. 2007. Percutaneous penetration enhancers: an overview. Skin Pharmacol Physiol 20: 272-282 and Benson H A 2005. Transdermal drug delivery: penetration enhancement techniques. Curr Drug Deliv 2: 23-33. In certain embodiments, recovery of the skin following removal of treatment at 7 days was monitored using TEWL (Example 6). Five sites were compared for the recovery and irritation studies. In addition to the treatment group and vehicle control, site 3 was used to evaluate the role of the NTX gel, site 4 was used to evaluate the effect of MN treatment, and site 5 was only occlusion used to control for TEWL enhancement at all sites due to occlusion alone. There was no significant difference among the sites following removal of treatment or at any of the later time points indicating that recovery of the skin was not influenced by the presence of FLU or ethanol. Recovery of the skin was expected, since removal of occlusion leads to increased TEWL across disrupted SC, which in turn acts as one of the major signals for lamellar body release and skin healing. See Li G, et al. 2010. Microchannels created by sugar and metal MNs: characterization by microscopy, macromolecular flux and other techniques. J Pharm Sci 99: 1931-41. Irritation data (Example 7) also indicated that there was no significant difference among the sites and $\Delta a^*$ values, and all sites were much lower compared to the positive control in HGP, the most sensitive model for skin irritation for transdermal and topical studies.

In other embodiments, staining studies (Example 8) were conducted to visualize the micropores at the end of the 7-day period. The studies were used as a visualization technique for presence of micropores for correlation with PK data. The studies indicated that micropores could be visualized in FLU treated groups; however they were not present for the ethanol control group at 7 days. NTX concentration in the plasma of the ethanol treated group was <2 ng/ml at 7 days, probably indicating that micropores had resealed by that time. The FLU treated group showed additional staining in the regions between the micropores.

Methods of Treating Alcohol and Opioid Addiction

Described herein are methods of treating one or more medical conditions (i.e., alcohol or opioid addiction) in a mammal by transdermally delivering an active pharmaceutical agent through the pores created by a MN array which has penetrated the skin of a mammal and the resulting pores have been kept suitably viable for the delivery of an active pharmaceutical agent by the topical use of a lipid biosynthesis inhibitor in conjunction with the use of a MN array.

In other embodiments the lipid biosynthesis inhibitor can be a HMG-CoA reductase inhibitor such as FLU. In a further embodiment the lipid biosynthesis inhibitor can be in any pharmaceutically acceptable form. In yet other embodiments, transdermal administration of an active pharmaceutical agent may be in the form of an abuse-resistant formulation. The medical condition to be treated is not limited and can be any condition for which the active pharmaceutical agent required for treatment can be delivered transdermally by use of a MN array and a lipid biosynthesis inhibitor as described herein. By way of example, and without limitation to treatment of alcohol and opioid addiction as described herein, the medical condition to be treated can include: pain disorders, cardiovascular disorders, respiratory disorders, gastrointestinal disorders, renal disorders, psychiatric disorders, endocrinological, gynecological and obstetric disorders, immunological disorders, bone and joint disorders, hematological disorders, oncologic disorders, nutritional disorders, and infectious diseases. The use of specific active pharmaceutical agents to treat the exemplified disorders is known in the skill in the art, as exemplified in The Physicians Desk Reference, 58.sup.th Ed., and Goodman and Gilmans, "The Pharmacological Basis of Therapeutics, 11th Ed.

The terms "treat", "treated", "treating" and "treatment" are to be broadly understood as referring to any response to, or anticipation of, a medical condition in a mammal, particularly a human, and includes but is not limited to: (i) preventing the medical condition from occurring in a subject, which may or may not be predisposed to the condition, but has not yet been diagnosed with the condition and, accordingly, the treatment constitutes prophylactic treatment for the medical condition; (ii) inhibiting the medical condition, i.e., arresting, slowing or delaying the onset, development or progression of the medical condition; or (iii) relieving the medical condition, i.e., causing regression of the medical condition.

In certain embodiments, the active pharmaceutical agent or µ-opioid receptor antagonist, NTX, may be used transdermally in MN-treated skin for treatment or reduction of opioid or alcohol addiction. The currently approved dosage forms of NTX include oral and an extended release intramuscular injection. The oral dosage form has issues with variable bioavailability and compliance in its treatment population due to daily dosing and side effects. The extended-release intramuscular injection is difficult to remove if there is a need for emergency opiate treatment, and also leads to injection site reactions. Thus NTX is suitable for transdermal patch development and an active delivery system in the form of MNs since the drug cannot be delivered in therapeutic concentrations via passive delivery.

It has been previously shown that by using MNs, NTX can be delivered at therapeutic levels for 2-3 days in humans. In certain embodiments, with the addition of an HMG-CoA reductase inhibitor (i.e., FLU), enhancement of drug delivery to 7 days was achieved. Therefore, methods of treating opioid or alcohol addiction are provided.

Treatment of alcohol and opioid addiction preferably involves topical application of therapeutically effective amounts of one or more active agents or pharmaceutical formulations comprising them to MN-treated skin. The HMG-CoA reductase inhibitors (e.g., FLU)+µ-opioid receptor antagonist (e.g., NTX) described herein are referred to as "inhibitory agents" and "active agents," respectively. The amount of active agent will vary depending on many factors, including the severity of the addiction, the age, sex, and immune status of the subject. As described above, in preferred embodiments, therapeutically effective amounts of the HMG-CoA reductase inhibitor FLU range 0.1 to 10 mg/cm$^2$, preferably 0.6 mg/cm$^2$. Therapeutically effective amounts of the μ-opioid receptor antagonist NTX gel range from about 10 to 100 mg/cm$^2$, preferably 27 mg/cm$^2$ NTX gel. Various factors known to those skilled in the art affect the actual therapeutic amounts used in vivo, especially in humans. Higher or lower doses may also be effective as is discussed herein. Penetration of the active agents transdermally can be optimized by adjusting the dose, but also by formulating the active agents in ways that enhance uptake.

In an embodiment of the invention, healthy subjects are treated by contacting and inserting into the skin a MN-array to generate non-overlapping MN pores. The MN-array is rotated at an angle, preferably about 45 degrees, following the first insertion to ensure non-overlapping pores and held in place for a specified period of time (e.g., 15-20 seconds) for each application. FLU is deposited topically using an ethanol solution and then followed by treatment topically with NTX gel. All sites are occluded using patches for 7 days following treatment to achieve average therapeutically effective plasma concentrations. The present therapies can be used in conjunction with other therapies that are well-known in the art and are effective in treating alcohol or opioid addiction. Preferably the subject is human.

Abuse-Deterrent Transdermal Formulations

Also described herein are abuse-resistant multi-layer transdermal patches comprising opioids and opioid prodrugs having a barrier layer located between the layer containing the opioid or opioid prodrug and a layer containing a lipid biosynthesis inhibitor and an opioid antagonist or opioid antagonist prodrug.

In one embodiment, an abuse-resistant patch for transdermally delivering an opioid to a subject is provided. It comprises a backing layer and a first layer underlying the backing layer. This first layer comprises an opioid antagonist or opioid antagonist prodrug which is not transdermally delivered at therapeutic levels when the patch is used for transdermally administering the opioid to the subject. The backing layer is substantially impermeable to the opioid antagonist or opioid antagonist prodrug of the first layer. The abuse-resistant patch further comprises a second layer underlying the first layer. The second layer comprises a lipid biosynthesis inhibitor, an opioid antagonist and a pressure sensitive adhesive; wherein the second layer is adapted to be in diffusional communication with the skin of the subject to transdermally administer a therapeutically effective amount of the opioid antagonist to the subject. A barrier layer is provided and located between the first and second layer. It comprises a water-insoluble polymeric material and a water-soluble polymer where the release ratio is between about 1:60 and about 60:1 after the patch has been placed in ethanol, water, or a phosphate buffer having a pH of about 6.5 for greater than about 30 seconds.

The abuse-resistant transdermal patch comprises an opioid antagonist, selected from the group consisting of buprenorphine, clonidine, estradiol, estradiol and levonorgestrel, estradiol and norethindrone acetate, ethinyl estradiol and norelgestromin, fentanyl, granisetron, methylphenidate, naltrexone HCL, nicotine, nitroglycerin, oxybutynin, oxybutynin chloride, rivastigmine, scopolamine, selegiline, testosterone, capsaicin, diclofenac epolamine, diclofenac sodium, lidocaine, lidocaine and prilocaine, lidocaine and tetracaine, methylphenidate, menthol and capsaicin, menthol and methyl salicylate, salicylic acid, rivastigmine, rotigotine, scopolamine, and trolamine salicylate. The opioid antagonist is preferably naltrexone or naloxone.

Furthermore, the abuse-resistant transdermal patch comprises a lipid biosynthesis inhibitor, preferably a HMG-CoA reductase inhibitor selected from the group consisting of: atorvastatin, fluvastatin, pitavastatin, pravastatin, rosuvastatin, and simvastatin.

Methods of making an abuse-resistant transdermal patch for delivering an opioid to a subject are also provided in certain embodiments and comprise (a) applying a first layer to a substrate comprising a backing layer, the backing layer comprising: an opioid antagonist which is not transdermally delivered at therapeutic levels when the patch is used for transdermally administering the opioid; (b) applying a barrier layer to the first layer, the barrier layer comprising: a water-insoluble polymeric material and a water-soluble polymer; and (c) applying a second layer to the barrier layer, the second layer comprising (i) a lipid biosynthesis inhibitor (ii) an opioid antagonist; and a (iii) a pressure sensitive adhesive; wherein the second layer is adapted to be in diffusional communication with the skin of the subject to transdermally administer a therapeutically effective amount of the opioid antagonist to the subject wherein the release ratio is between about 1:60 and about 60:1 after the patch has been placed in ethanol, water, or a phosphate buffer having a pH of about 6.5 for greater than about 30 seconds.

The non-reactive backing layer may be an occlusive backing, such as Cotran 9715 Film 3M™ Underlying the non-reactive backing layer is the opioid antagonist (or prodrug thereof) layer. Next, the barrier layer separates the opioid antagonist (or prodrug thereof) layer from the opioid agonist/agonist-antagonist (or prodrugs thereof) layer. In one embodiment, the barrier layer is a polymeric film or mixture of polymers that is substantially impermeable to opioid antagonists, opioid agonists and opioid agonist-antagonists thereby functioning to separate the contents of layer from layer. The opioid agonist/agonist-antagonist (or prodrug thereof) layer contains an opioid agonist, an opioid agonist-antagonist, an opioid agonist prodrug or an opioid agonist-antagonist prodrug. A removable film covering may be used. Illustratively, Scotch Pack 1022 Release Liner 3.0 mil 3M™ may be used as a film covering. Prior to administration to a subject, the film covering is removed and layer is placed in direct contact with the subject's skin. In certain embodiments, the thickness of the opioid antagonist and opioid agonist/agonist-antagonist layer may be increased to achieve longer wear time.

The opioid agonist for use can be selected from the group comprising alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine, tramadol and salts of the foregoing. In another embodiment, the composition comprises pharmaceutically acceptable prodrugs of opioid agonist.

In another embodiment, an opioid agonist-antagonist for use can be selected from the group comprising buprenorphine, butorphanol, dezocine, meptazinol, nalbuphine, nalorphine, pentazocine and salts of the foregoing. In a further embodiment, the opioid agonist or agonist-antagonist is buprenorphine. In another embodiment, the composition comprises pharmaceutically acceptable prodrugs of opioid agonist or agonist-antagonists.

In one embodiment, the opioid antagonist layer comprises an opioid antagonist selected from the group consisting of: NTX, 6-beta-naltrexol, nalbuphine, nalmefene, naloxone ("NLX"), cyclazocine, levallorphan, cyclorphan, oxilorphan and prodrugs of the foregoing. Also included herein are pharmaceutically acceptable forms including the free base, salt, ester, hydrate, polymorph and derivative of these compounds provided that the free base, salt, ester, hydrate, enantiomer, isomer, tautomer, polymorph or any other pharmacologically suitable derivative is, or becomes, a therapeutically active form of naltrexone. As described herein, prodrugs of naltrexone and/or naloxone can be used with or instead of naltrexone and/or naloxone, respectively.

In a further embodiment, the opioid antagonist/antagonist prodrug layer can further comprise a water-insoluble polymeric material and/or a water-soluble polymer used in preparing the barrier layer and described in further detail below. The water-insoluble polymeric material and/or a water-soluble polymer added can be materials suitable for use in the barrier layer, even though the materials are not actually present in a particular embodiment of the barrier layer. The barrier layer functions to separate the layers on either side of the barrier from contacting one another and to prevent the diffusion of opioid antagonist or opioid antagonist prodrug. In one embodiment the barrier layer is comprised of a polymeric film. In a further embodiment, the polymeric film is comprised of a mixture of a water-insoluble polymeric material and a water-soluble polymer. In a further embodiment, the water soluble polymer is suitable for forming pores or other openings in the water-insoluble polymeric material to allow the opioid antagonist (or prodrug thereof) a possible route of egress from layer of the transdermal patch upon misuse or abuse.

The water-insoluble polymeric material can be selected from the group consisting of: cellulose derivatives, such as ethyl cellulose (EC), cellulose esters, ethylene-vinyl acetate copolymer (EVA), polyolefins such as polyethylene, low density polyethylene (LDPE), medium density polyethylene (MDPE), high density polyethylene (HDPE), polypropylene, ethylene-propylene copolymers, styrene polymers such as polystyrene, vinyl polymers, polyvinyl acetate, and the like, acrylic polymers, such as ethylenemethyl acrylate copolymer, polymethyl acrylate, polyethyl acrylate, ethylene-acrylic acid copolymer, ethylene-ethylacrylate copolymer, homopolymers and copolymers of acrylic acid, methyl methacrylate and combinations thereof, and methyl acrylic acid esters with quaternary ammonium groups, such as Eudragit NE, RS, RL and the like. The water-insoluble polymeric material can also be combinations of the foregoing.

Water-soluble polymers suitable for use with the water-insoluble polymeric material for barrier layer are selected from the group consisting of: cellulose derivatives such as hydroxypropylcellulose (HPC), hydroxypropylmethylcellulose (HPMC), hydroxyethylcellulose (HEC), methyl cellulose (MC), cellulose gum, sodium carboxymethylhydroxyethylcellulose, methylhydroxyethylcellulose (MHEC), carboxyalkylcelluloses such as carboxymethylcellulose (CMC), Benecel®, Culminal®. polyvinylpyrrolidone (PVP), polyethylene oxide (PEO), polysaccharides such as dextran or polysialic acid (PSA), natural water-soluble polymers such as, corn starch, natural gums such as agar, agarose, alginates, xanthan gums, heparin, chitin, and chitosan, cellulose derivatives, polyvinyl alcohol, polyethylene glycol, polyoxazoline, poly acryloylmorpholine, and the like.

In a further embodiment, the barrier layer further includes a plasticizer. A suitable plasticizer can be selected from the group consisting of: polyethylene glycol, propylene glycol, di-n-butylphthalate, glycerol, triethyl citrate, dibutyl phthalate, diethyl phthalate, paraffinic process oils, naphthenic process oils, aromatic process oils, and the like, squalane, squalene, olive oil, camellia oil, castor oil, tall oil, peanut oil, silicone oils, mineral oil, oleyl alcohol and the like, dioctyl phthalate, and the like, polybutene, liquid isoprene rubber, isopropyl myristate, hexyl laurate, diethyl sebacate, diisopropyl sebacate, diethylene glycol, glycol salicylate, dipropylene glycol, triacetin, crotamiton and the like, glycerol, oleic acid, and the like.

The non-reactive backing layer is substantially impermeable to the opioid antagonist (or opioid antagonist prodrug) and other components of the multi-layer patch. Because the backing layer is substantially impermeable to the opioid antagonist (or opioid antagonist prodrug), it prevents diffusion or other transport of the opioid antagonist (or antagonist prodrug) through the backing layer even when the transdermal patch described herein has been placed in a solvent (e.g., water or ethanol) for attempted abuse or misuse of the transdermal patch. As used in association with the backing layer, the phrase "substantially impermeable" means that the contents of the transdermal patch (e.g., an opioid antagonist or opioid antagonist prodrug) are less likely to permeate, diffuse or otherwise transported through the backing layer and be separated from the transdermal patch. Further, even though the backing layer is substantially impermeable to the contents of the transdermal patch, some contents of the patch may pass through the backing layer; however, it is intended that the amount of material diffusing through the backing layer be negligible relative to the overall contents and function of the patch. Moreover, because the backing layer is substantially impermeable, any unintended diffusion through the backing layer would not be a significant route of material (e.g., the opioid antagonist or antagonist prodrug) leaving the patch under conditions of anticipated use (transdermal delivery of an opioid) or misuse/abuse (e.g., placing in a solvent such as water or alcohol to extract the opioid agonist) of the patch.

The backing layer may be made of a single layer or film of polymer, or be a laminate of one or more polymer layers. Preferably, the backing layer has high flexibility, good oxygen transmission and high moisture-vapor transmission rate. Non-limiting examples of polymers suitable for use in the backing layer are polyurethane, polyvinylchloride, polyvinylidene chloride, polyolefins such as ethylene-vinyl acetate copolymers, polyethylene, and polypropylene, and polyesters such as polyethyleneterephthalate. Additional examples of the backing layer include CoTran 9701 Film 3M™, CoTran 9702 Film 3M™, CoTran 9706 Film 3M™, CoTran 9715 Film 3M™, CoTran 9720 Film 3M™, CoTran 9722 Film 3M™, Foam Tape 9772L 3M™, Foam Tape 9773 3M™, Scotchpak™ 1006, Scotchpak™ 1109, Scotchpak™ 9723, Scotchpak™ 9732 and Scotchpak™ 9733.

The adhesive layers are formed from standard pressure sensitive adhesives known in the art. Non-limiting examples of pressure sensitive adhesives include polymer and copolymers of polyacrylates, polysiloxanes, polyisobutylene, polyisoprene, polybutadiene, ethylene-vinyl acetate and styrenic block polymers, such as styrene-isoprene-styrene block copolymer, styrene-butadiene-styrene copolymer, styrene-ethylenebutene-styrene copolymers, styrene-ethylene/propylene-styrene copolymers and di-block analogs thereof. Examples of polyacrylates include, but are not limited to, acrylic acids, alkyl acrylates and methacrylates; for example, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, vinylacetate/ethylene acrylate and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989).

Other useful pressure sensitive adhesives (PSA) can include mixtures of different polymers or mixtures of polymers such as synthetic rubber polyisobutylene (PIB), The PIB adhesives normally include a tackifier such as polybutene oil and resins such as the ESCOREZ® resins available from Exxon Chemical. Other useful rubber-based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof. Additional suitable pressure sensitive adhesives can be found in U.S. Pat. No. 7,867,986 which is hereby incorporated by reference in its entirety. Polyisobutylene polymers are available commercially under the trademark name VISTANEX® from Exxon Chemical.

Silicone-based pressure sensitive adhesives are also suitable for use in additional embodiments described herein. Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, N.Y. (1989), incorporated by reference in its entirety. Other useful silicone-based pressure sensitive adhesives are described in the following U.S. Pat. Nos. 4,591,622; 4,584,355; 4,585,836; and 4,655,767 which are hereby incorporated by reference in their entirety. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich. The commercially available silicones are sold under the trademark of BIO-PSA such as Bio-PSA 7-4102, 7-4202, 7-4302, 7-4101, 7-4201, 7-4301, 7-4303, 7-4503, 7-4603 by Dow Corning Cooperation. In one embodiment, amine-compatible Bio-PSA silicone adhesives are preferred. In a further embodiment, the preferred amine-compatible Bio-PSA silicone adhesive 7-4202 was employed in combination with acrylic adhesive such as Duro-tak 87-9301 manufactured by National Starch and Chemical Company.

In one embodiment a pressure sensitive adhesive is optionally used to assist in affixing a patch containing an opioid to be transdermally delivered to the subject. In a further embodiment, the pressure sensitive adhesive is present in a total amount by weight between about 1% and about 99.9%; between about 50% and about 99.9% and between about 75% and about 99.9%. In a further embodiment the pressure sensitive adhesive layer is a mixture of two or more pressure sensitive adhesives. In another embodiment, the pressure sensitive adhesive is a mixture of Bio-PSA silicone adhesive 7-4201 and Duro-Tak 87-9301 (manufactured by Dow Corning Corporation, Medical Products, Midland, Mich. and the National Starch and Chemical Company, respectively) which are mixed in a ratio of about 10:1 (7-4202:87-9301).

The removable film covering is a protective layer made of a polymeric material that may be optionally metalized. Examples of polymeric materials include, but not limited to, polypropylene, polystyrene, polyurethane, polyethylene, polyimide, polyethylene terephthalate, polybutylene terephthalate, polyvinyl chloride, ethyl vinyl acetate, paper and the like. Illustratively, Scotch Pack 1022 Release Liner 3.0 mil 3M™ and Scotch Pack 9742 Release Liner 3M™.

Kits

In other embodiments of the invention, various kits are also provided. Typically, the kits include a pharmaceutical composition as described herein and instructions for the use of the pharmaceutical composition and dosage regime. The kit can comprise the pharmaceutical composition of the invention in a suitable container with labeling and instructions for use. The container can be, but is not limited to, a dropper or tube. The pharmaceutical composition of the invention can be filled and packaged into a plastic squeeze bottle or tube. Suitable container-closure systems for packaging pharmaceutical compositions of the invention are commercially available for example, from Wheaton Plastic Products, 1101 Wheaton Avenue, Millville, N.J. 08332.

Preferably, instructions are packaged with the formulations of the invention, for example, a pamphlet or package label. The labeling instructions explain how to administer pharmaceutical compositions of the invention, in an amount and for a period of time sufficient to treat or prevent any symptoms associated therewith. Preferably, the label includes the dosage and administration instructions, the pharmaceutical composition, the clinical pharmacology, drug resistance, pharmacokinetics, absorption, bioavailability, and contraindications.

5. Examples

Embodiments are illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description.

Although specific terms are employed, they are used as in the art unless otherwise indicated.

Example 1: Methods and Materials

Materials

Naltrexone HCL was purchased from Mallinckrodt (St. Louis, Mo.), and fluvastatin sodium from Cayman chemical (Ann Arbor, Mich.). Propylene glycol and ethanol (200 proof) were purchased from Sigma (St. Louis, Mo.). Acetic acid, ammonium acetate and benzyl alcohol were obtained from Fisher Scientific (Fair Lawn, N.J.). 1-Octanesulfonate, sodium salt was obtained from Regis Technologies, Inc (Morton Grove, Ill.). Trifluroacetic acid (TFA), triethylamine (TEA), methanol, ethyl acetate and acetonitrile (ACN) were obtained from EMD chemicals (Gibbstown, N.J.). Natrosol® (hydroxyethlycellulose) was obtained from Ashland (Wilmington, Del.). Ethanol (70%) was obtained from Ricca chemical (Arlington, Tex.). Sterile water for injection was from Hospira (Lake Forest, Ill.) and water was purified using a NANOpure Diamond™, Barnstead water filtration system for all in vitro experiments.

HPLC Methods

NTX and FLU were quantified using high pressure liquid chromatography (HPLC). The HPLC system consisted of a Waters 717 plus auto-sampler, a Waters 600 quaternary pump, and a Waters 2487 dual wavelength absorbance detector with Waters Empower™ software. A Perkin Elmer Brownlee™ Spheri 5 VL C18 column (5μ, 220×4.6 mm) and a C18 guard column (15×3.2 mm) were used with the UV detector set at a wavelength of 280 nm for NTX and 305 nm for FLU. The mobile phase consisted of 65:35 (v/v) ACN: (0.1% TFA with 0.065% 1-octane sulfonic acid sodium salt, adjusted to pH 3.0 with TEA aqueous phase). Samples were run at a flow rate of 1.5 ml/min. The injection volume used was 1000 for all samples.

Statistical Analysis

Data for all experiments are reported as mean±standard deviation. Statistical analysis of data was carried out with Students' t-test and one way ANOVA with post hoc Tukey's pairwise tests, if required, using GraphPad Prism® software, version 0.04 software. P<0.05 was considered to be statistically significant.

Example 2: In Vitro Experiments

In vitro studies were performed to look at the flux across MN treated skin and the skin concentrations of NTX and FLU in the skin. Full-thickness Yucatan miniature pig skin was used for all in vitro experiments. All pig tissue harvesting experiments were done under IACUC approved protocols at the University of Kentucky. Fresh skin was cleaned to remove excess subcutaneous fat, dermatomed and stored at −20° C. Skin was thawed and cut into small square pieces on the day of the diffusion experiment. The thickness was measured for each individual piece of skin and the average thickness of all treatment groups was maintained between 1.4-1.8 mm. Skin was next treated with a 5 MN in-plane array, 10 times in one direction and 10 times in a mutually perpendicular direction to generate a total of 100 MN insertions within the active treatment area of 0.95 $cm^2$. Five treatment groups were used based on the 4 different vehicles used for FLU and a control for NTX only; all studies were done in triplicate. Saturated NTX gel was prepared by mixing 90 mg/mL of NTX HCL (saturated solution) with propylene glycol (PG) (10%). A 3% HEC gel of the NTX solution was used for the in vitro studies. The four different FLU treatments were FLU in 200 proof ethanol, acetone, PG:ethanol=7:3 and PG:ethanol:water=1:2:1. All the vehicles for FLU were based on previous studies looking at recovery of the skin or commonly used drug deposition methods. See Elias P M, et al. 2002. The Potential of Metabolic Interventions to Enhance Transdermal Drug Delivery. J Investig Dermatol Symp Proc 7: 79-85 and Li Y Z, et al., 2012. The concentration of FLU was 1.5% for all the formulations and 40 μl of the formulation was applied to each cell. The receiver solution was water alkalified to pH 7.4 containing 20% ethanol at 37° C. to mimic physiological conditions. The temperature of the diffusion cell skin surface was maintained at 32° C. Samples were collected every 6 h for 48 h. All samples were analyzed using HPLC. The steady state flux of NTX was calculated using the steady state portion of the cumulative amount permeated vs. time plot. The skin concentrations of both drugs were also determined at the end of the study by extracting the drug overnight into 10 mL of ACN, and injecting the extracted sample onto the HPLC column after appropriate dilutions.

The in vitro diffusion studies were carried out to optimize the formulations for in vivo studies. All formulations for FLU were chosen based on previous publications on skin recovery following FLU treatment. The NTX was formulated in 10% PG containing formulation because concentrations higher than 10% of PG have been shown to decrease flux across MN treated skin significantly. See Ghosh P. et al., 2013. The in vitro results as shown in FIG. 1A-1B indicate that there was no significant difference in flux across MN treated skin among the 5 different treatment groups ($p>0.05$). The skin concentration data indicated that there was no significant difference in the concentration of NTX or FLU in the skin irrespective of the method of FLU deposition ($p>0.05$). Ethanol (200 proof) was chosen as the vehicle for FLU deposition from these studies.

Example 3: Pharmacokinetic Studies

Pharmacokinetic (PK) studies were carried out in hairless guinea pigs (HGP) using FLU and NTX to evaluate the effectiveness of FLU as a pore lifetime enhancement technique. All animal studies were approved by the IACUC at University of Kentucky and University of Maryland. All animals used had jugular vein catheters. Catheters were either implanted in the laboratory or animals were purchased with catheters from Charles River. Three treatment groups were used for the PK studies. Treatment group: 300 μL of NTX gel+40 μL of FLU in ethanol (200 proof), vehicle control group: 300 μL of NTX gel+40 μL of ethanol (200 proof), MN control group: 200 μL of NTX gel. For PK studies, preparation of the NTX gel was similar to the in vitro studies except 1% benzyl alcohol was added as an antibacterial agent. All sites were treated twice with a 50 MN array to generate a total of 100 MN pores and there were 2 treatment sites per animal. FLU was deposited using the ethanol solution in the active treatment group; only ethanol was used in the vehicle control group followed by NTX gel for all three groups. All sites were occluded using patches for 7 days following treatment. Two hundred μl blood samples were withdrawn from the catheter at regular intervals into collection tubes precoated with 500 IU/mL heparin. The blood samples were immediately centrifuged at 10,000×g for 3 min; plasma was separated and stored at −80° C. until analysis. All in vivo studies were carried out at least in triplicate. Data for control studies were previously reported in Nicole Brogden's thesis at the University of Kentucky.

The pharmacokinetic studies were carried out to evaluate the effect of FLU treatment on micropore closure in vivo in a HGP model. The three treatment groups were evaluated either for 168 h for the treatment and vehicle control groups, or for 96 h for MN control. The results as shown in FIG. 2A-2B indicate that detectable levels of NTX were present in the plasma for 72 h for all study groups. The average plasma concentration for the MN only control was below 2 ng/mL beyond 58 h. The plasma concentrations from vehicle control treatments were below 2 ng/mL beyond 144 h, and plasma concentrations for FLU treatment group were above 2 ng/mL throughout the range of the study. The WinNonlin parameters shown in Table 1 indicated that the areas under the curves (AUC) for plasma concentration vs. time plots were not significantly different from each other for the treatment group and the vehicle control group (p>0.05). There was no lag time observed with MN enhanced delivery in any of the three groups. There was no significant difference in maximum drug concentration ($C_{max}$) among the 3 groups (p>0.05). The average plasma concentration was 39.2±15.4 ng/mL. $T_{max}$ or time to maximum plasma concentration was reached between 15 minutes and 4 hours for all studies. The standard curves in ACN and plasma were linear in the range on 1-75 ng/mL, $r^2 \geq 0.98$.

TABLE 1

WinNonlin parameters from pharmacokinetic studies

| | Treatment group | Vehicle control | MN control |
|---|---|---|---|
| $C_{max}$(ng/mL) | 38.1 ± 19.7 | 39.3 ± 19.2 | 39.4 ± 11.5 |
| $T_{max}$(h) | 2.7 ± 3.8 | 1.4 ± 1.7 | 2.8 ± 2.0 |
| AUC (ng*h/mL) | 1411.1 ± 1040.5 | 1696.1 ± 1665.8 | 613.5 ± 212.9 |
| (time for AUC | (146.7 ± 24.4) | (151.0 ± 25.7) | (80.0 ± 13.9) |
| $C_{ss}$ (ng/mL) | 9.3 ± 5.6 | 11.1 ± 9.7 | 7.5 ± 1.5 |
| n | 3 | 4 | 3 |

Example 4: LC/MS-MS Analysis of Plasma Samples

All plasma samples were extracted using a previously validated method. See Ghosh P. et al. 2013. Five hundred μL of 1:1 ACN: ethyl acetate was added to 100 μL of plasma for protein precipitation. The mixture was vortexed for 15 seconds and centrifuged for 20 minutes at 12000×g. The supernatant was removed carefully without disturbing the pellets and dried under nitrogen in a glass test tube. The extract was suspended in 100 μL ACN, vortexed, sonicated for 10 minutes and transferred to HPLC vials with low-volume inserts for injection. For plasma standards, the 100 μL of the blank plasma was spiked with 10 μL of ACN standards and extracted following the same method as above.

The LC/MS-MS system consisted of HPLC Waters Alliance 2695 Separations Module, Waters Micromass® Quattro Micro™ API Tandem Mass Spectrometer and Masslynx Chromatography software with Waters Quanlynx (V. 4.1) analysis software. A Waters Atlantis Silica HILIC column (5 μm, 150×2.1 mm) and guard column (10×2.1 mm) were used for LC separation. The mobile phase composition was methanol with 0.1% acetic acid: 20 mM ammonium acetate=95:5, the flow rate was 0.5 ml/min and positive mode atmospheric pressure chemical ionization was used for detection of NTX (APCI+). Multiple reaction monitoring (MRM) was carried out with the following parent to daughter ion transitions for NTX.HCl m/z 341.8→323.8. The corona voltage was 3 μA, cone voltage 25 V, extractor 2 V, RF lens 0.3 V, source temp 130° C., APCI probe temperature 575° C. The collision gas was 20 eV. Nitrogen gas was used as a nebulization and drying gas at flow rates of 50 and 3501/h, respectively. Injection volume was 40 μL.

Example 5: Pharmacokinetic Analysis

The plasma concentration vs. time data obtained using the MS were modeled by fitting data to a non-compartmental model with extravascular output (WinNonlin Professional, version 4.0, Pharsight Corporation, Mountain View, Calif.) to obtain pharmacokinetic parameters like area under the curve (AUC), maximum plasma concentration ($C_{max}$) and time to maximum plasma concentration ($T_{max}$).

Example 6: Reversibility/Recovery of Pores

The reversibility/recovery of the pores following removal of occlusion was studied using transepidermal water loss (TEWL) in a HGP model. Five different sites were chosen on the dorsal region of an animal. The treatment sites were site 1: MN+NTX gel+FLU (200 proof ethanol), site 2: MN+NTX gel+200 proof ethanol, site 3: MN+placebo gel, site 4: no MN treatment+placebo gel and site 5: occlusion only. All sites were marked and cleaned on the day of the treatment. Sites 1, 2 and 3 were treated twice, with 50 MN arrays (620 μm), (the two treatments being mutually perpendicular to each other to give a total of 100 nonoverlapping insertions) and TEWL readings were obtained before and immediately following treatment at all sites using a TEWL evaporimeter (cyberDERM, Media, Pa.). The concentration and amount of NTX gel and FLU were consistent with the PK studies. A placebo gel was used for site 3 and site 4. The placebo gel was similar in composition to the NTX gel with 10% PG, 1% benzyl alcohol and 3% HEC as the gelling agent. Forty μL of the 1.5% FLU in ethanol or 200 proof ethanol was applied to the treated skin at site 1 and 2, respectively and 300 μL of NTX/placebo was applied to sites 1-4. All sites were occluded using a transdermal patch (148) secured in place with Bioclusive™ tape. The occlusive patch was removed after 7 days and TEWL measurements were obtained for 30-45 min at all sites or until values returned to baseline (pretreatment values). All experiments were conducted at least in triplicate.

Recovery of the skin, (i.e., regeneration of the barrier function of the SC) was studied using TEWL. These studies were carried out to look at the effect of the local concentration of FLU on the recovery/healing of the skin following removal of occlusion. The recovery data (FIG. 3) were represented as a ratio of the post treatment values to the pretreatment intact skin/baseline values. Values with an enhancement ratio of less than 1 were not used for the calculation since values below baseline indicates complete reversal of treatment. The recovery studies indicated that there were no significant differences among the 5 treatment groups used for the recovery studies (p>0.05).

Example 7: Skin Irritation

Local skin irritation can be one of the major drawbacks of topical/transdermal delivery, so irritation studies were conducted to look at the effect of local FLU treatment of the skin in HGP. The studies were conducted using the same treatment groups as the recovery studies. Colorimeter (Chroma Meter CR-400, Konica, Minolta, Japan) readings were obtained, in triplicate, at each site before and immediately after the treatment. The data were used to record changes in the color of the skin from baseline based on 3 different color axes, the red-green axis (a*), the black-white axis (L*) and the yellow-blue axis (b*). The sites were then occluded for 7 days and readings were obtained after removal of occlusion. The degree of redness of the skin or the change in erythema of the skin was measured by the change in the red green axis (Δa*) values. Skin irritation studies were conducted in triplicate.

The irritation studies were carried out to look at the effect of local FLU treatment on the skin at 7 days. The data as shown in (FIG. 4) indicated that there were no significant differences among the treatment groups immediately following treatment or following removal of the patches at 7 days following treatment (p>0.05). The established positive control treatment for irritation studies in HGP is 0.5% sodium lauryl sulfate solution and the corresponding Δa* value is 12.3 (170). All the experimental values were significantly lower (p<0.05)

Example 8: Staining/Pore Visualization Studies

Pore visualization studies were carried out to look at the pores on the skin following treatment with FLU. Two sites were used on the same animal for these studies. Site 1: MN+NTX gel+FLU (200 proof ethanol) and site 2: MN: NTX gel+200 proof ethanol. The amount and concentration of all gels were consistent with the other studies. The skin was occluded for 7 days following treatment. Gentian violet was used to stain the skin after removal of the occlusive patch. The dye stains viable epidermis and not SC, so a grid can be clearly visualized for MN treatment/presence of micropores in the skin, whereas no staining can be observed on skin with intact SC.

The staining studies (FIG. 5A-5C) indicated that pores were present in the FLU treated group at the end of the 7-day patch application period compared to the absence of pores in the ethanol treated vehicle control group. In some of the studies staining was observed in the region surrounding the micropores for the treatment group. FLU is a known inhibitor of the cholesterol synthesis pathway; therefore it can influence the normal turnover of the intact skin in addition to the healing of the micropores. This process can lead to staining of the regions around the micropores.

In the present specification, the embodiments have been described with reference to certain specific embodiments. It will, however, be evident that various modifications and changes may be made thereto without departing from the broader spirit and scope. The specification and drawings are, accordingly, to be regarded in an illustrative rather than a restrictive sense. Although specific terms are employed, they are used as in the art unless otherwise indicated.

REFERENCES

All citations (e.g., scientific journal publications, patents, and other reference material) mentioned herein are hereby incorporated herein by reference to the same extent as if each individual citation was specifically and individually indicated to be incorporated by reference.
1. Flynn G L. 1996. Cutaneous and transdermal delivery: Processes and systems of delivery. 3rd ed. Dekker, New York: Modern Pharmaceutics.
2. Paudel K S, Milewski M, Swadley C L, Brogden N K, Ghosh P, Stinchcomb A L. 2010. Challenges and opportunities in dermal/transdermal delivery. Ther Deliv 1:109-131.
3. Elias P M, Tsai J, Menon G K, Holleran W M, Feingold K R. 2002. The potential of metabolic interventions to enhance transdermal drug delivery. J Investig Dermatol Symp Proc 7:79-85.
4. Tsai J C, Guy R H, Thornfeldt C R, Gao W N, Feingold K R, Elias P M. 1996. Metabolic approaches to enhance transdermal drug delivery.
1. Effect of lipid synthesis inhibitors. J Pharm Sci 85:643-648.
5. Harris I R, Farrell A M, Grunfeld C, Holleran W M, Elias P M, Fein-gold K R. 1997. Permeability barrier disruption coordinately regulates mRNA levels for key enzymes of cholesterol, fatty acid, and ceramide synthesis in the epidermis. J Investig Dermatol 109:783-787
6. Menon G K, Feingold K R, Elias P M. 1992. Lamellar body secretory response to barrier disruption. J Investig Dermatol 98:279-289.
7. Grubauer G, Feingold K R, Harris R M, Elias P M. 1989. Lipid content and lipid type as determinants of the epidermal permeability barrier. J Lipid Res 30:89-96.
8. Prausnitz M R. 2004. MNs for transdermal drug delivery. Adv Drug Deliv Rev 56:581-587
9. Prausnitz M R, Mitragotri S, Langer R. 2004. Current status and future potential of transdermal drug delivery. Nat Rev Drug Discov 3:115-124.
10. Prausnitz M R, Langer R. 2008. Transdermal drug delivery. Nat Biotechnol 26:1261-1268.
11. Davis S P, Martanto W, Allen M G, Prausnitz M R. 2005. Hollow metal MNs for insulin delivery to diabetic rats. IEEE Trans Biomed Eng 52:909-915.
12. Gill H S, Prausnitz M R. 2007. Coated MNs for transdermal delivery. J Control Release 117:227-237.
13. Henry S, McAllister D V, Allen M G, Prausnitz M R. 1998. Microfabricated MNs: A novel approach to transdermal drug delivery. J Pharm Sci 87:922-925.
14. Martanto W, Moore J, Kashlan O, Kamath R, Wang P, O'Neal J, Prausnitz M. 2006. Microinfusion using hollow MNs. Pharm Res 23:104-113.
15. Wermeling D P, Banks S L, Hudson D A, Gill H S, Gupta J, Prausnitz M R, Stinchcomb A L. 2008. MNs permit transdermal delivery of a skin-impermeant medication to humans. Proc Natl Acad Sci USA 105:2058-2063.
16. Daddona P, Matriano J, Mandema J, Maa Y F. 2011. Parathyroid hormone (1-34)-coated M N patch system: Clinical pharmacokinetics and pharmacodynamics for treatment of osteoporosis. Pharm Res 28:159-165.
17. Zhang Y, Brown K, Siebenaler K, Determan A, Dohmeier D, Hansen K. 2012. Development of lidocaine-coated M N product for rapid, safe, and prolonged local analgesic action. Pharm Res 29:170-177.
18. Banks S, Paudel K, Brogden N, Loftin C, Stinchcomb A. 2011. Diclofenac enables prolonged delivery of naltrexone through MN-treated skin. Pharm Res 28:1211-1219.
19. Gupta J, Gill H S, Andrews S N, Prausnitz M R. 2011. Kinetics of skin resealing after insertion of MNs in human subjects. J Control Release 154:148-155.
20. Kalluri H, Banga A. 2011. Formation and closure of microchannels in skin following microporation. Pharm Res 28:82-94.
21. Banks S L, Pinninti R R, Gill H S, Paudel K S, Crooks P A, Brogden N K, Prausnitz M R, Stinchcomb A L. 2010. Transdermal delivery of naltrexol and skin permeability lifetime after M N treatment in hairless guinea pigs. J Pharm Sci 99:3072-3080.
22. Brogden N K. 2012. Clinical evaluation of novel methods for extending M N pore lifetime. PhD. Thesis University of Kentucky.

23. Grubauer G, Elias P M, Feingold K R. 1989. Transepidermal water loss: The signal for recovery of barrier structure and function. J Lipid Res 30:323-333.
24. Micromedex2.0. Accessed Jul. 1, 2013, at: http://www-.micromedexsolutions.com/micromedex2/librarian.
25. Vivitrol. Alkermes. Accessed Jul. 1, 2013, at: http://www.vivitrol.com/.
26. Revia. Accessed Jul. 1, 2013, at: http://www.rxlist.com/revia-drug.htm.
27. Mao-Qiang M, Feingold K R, Thornfeldt C R, Elias P M. 1996. Optimization of physiological lipid mixtures for barrier repair. J Investig Dermatol 106:1096-1101.
28. Paudel K S, Nalluri B N, Hammell D C, Valiveti S, Kiptoo P, Hamad M O, Crooks P A, Stinchcomb A L. 2005. Transdermal delivery of naltrexone and its active metabolite 6-beta-naltrexol in human skin in vitro and guinea pigs in vivo. J Pharm Sci 94:1965-1975.
29. Milewski M. 2011. M N-assisted transdermal delivery of naltrexone species: In vitro permeation and in vivo pharmacokinetic studies. PhD. Thesis. Lexington, Ky.: University of Kentucky.
30. Milewski M, Stinchcomb A. 2011. Vehicle composition influence on the M N-enhanced transdermal flux of naltrexone hydrochloride. Pharm Res 28:124-134.
31. Andersen F, Hedegaard K, Petersen T K, Bindslev-Jensen C, Fuller-ton A, Andersen K E. 2006. The hairless guinea-pig as a model for treatment of cumulative irritation in humans. Skin Res Technol 12: 60-67.
32. Brogden N K, Milewski M, Ghosh P, Hardi L, Crofford L J, Stinch-comb A L. 2012. Diclofenac delays micropore closure following M N treatment in human subjects. J Control Release 163:220-229.
33. Brogden N, Banks S, Crofford L, Stinchcomb A. 2013. Diclofenac enables unprecedented week-long M N-enhanced delivery of a skin impermeable medication in humans. Pharm Res 30:1947-1955.
34. Ghosh P, Pinninti R R, Hammell D C, Paudel K S, Stinchcomb A L. 2013. Development of a codrug approach for sustained drug delivery across M N-treated skin. J Pharm Sci 102:1458-1467.
35. Ghosh P. 2013. Formulation optimization for pore lifetime enhancement and sustained drug delivery across M N treated skin. PhD. Thesis. Lexington, Ky.: University of Kentucky.
36. American Chemical Society. Accessed Jul. 1, 2013. www.scifinder.cas.org.
37. Kurihara-Bergstrom T, Knutson K, DeNoble L J, Goates C Y. 1990. Percutaneous absorption enhancement of an ionic molecule by ethanol-water systems in human skin. Pharm Res 7:762-766.
38. Barry B W. 1987. Mode of action of penetration enhancers in human skin. J Control Release 6:85-97.
39. Thong H Y, Zhai H, Maibach H I. 2007. Percutaneous penetration enhancers: An overview. Skin Pharmacol Physiol 20:272-282.
40. Arora A, Kisak E, Karande P, Newsam J, Mitragotri S. 2010. Multicomponent chemical enhancer formulations for transdermal drug de-livery: More is not always better. J Control Release 144:175-180.

The invention claimed is:

1. A transdermal drug delivery system for transdermal delivery of an active pharmaceutical agent to microneedle-treated skin of a subject for up to 7 days, comprising:
 (a) a topical formulation for one-time application to skin of the subject, comprising a pharmaceutically acceptable topical carrier and a lipid biosynthesis inhibitor compound, and an active pharmaceutical agent for transdermal delivery to the subject; and
 (b) optionally, a microneedle array which produces a plurality of micropores that breach at least the stratum corneum of the skin of the subject;
 wherein the topical formulation is formulated to be administered to skin of the subject one time in 7 days, before, after or during microneedle treatment of the skin to produce micropores that breach at least the stratum corneum of the skin, and
 wherein healing or resealing of the micropores in the microneedle-treated skin is delayed for longer than 72 hours and up to 7 days such that the transdermal drug delivery system delivers a pharmaceutically effective and sustained dose of the active pharmaceutical agent over a period of at least 72 hours.

2. The transdermal drug delivery system of claim 1, wherein the lipid biosynthesis inhibitor is selected from the group consisting of fatty acid synthesis inhibitors, cholesterol synthesis inhibitors and ceramide synthesis inhibitors.

3. The transdermal drug delivery system of claim 1, wherein the lipid biosynthesis inhibitor is selected from the group consisting of 5-(tetradecycloxy)-2-furancarboxylic acid (TOFA), HMG-CoA reductase inhibitors, and β-chloralanine (BCA).

4. The transdermal drug delivery system of claim 3, wherein the HMG-CoA reductase inhibitor is selected from a group consisting of: atorvastatin, fluvastatin, pitavastatin, pravastatin, rosuvastatin, and simvastatin.

5. The transdermal drug delivery system of claim 4, wherein the HMG-CoA reductase inhibitor is fluvastatin and is administered in an amount in a range from about 0.1 to 10 mg/cm$^2$.

6. The transdermal drug delivery system of claim 5, wherein the fluvastatin is administered in an amount of 0.6 mg/cm$^2$.

7. The transdermal drug delivery system of claim 1, wherein the active pharmaceutical agent is selected from the group consisting of buprenorphine, clonidine, estradiol, fentanyl, granisetron, methylphenidate, naltrexone HCL, nicotine, nitroglycerin, oxybutynin, oxybutynin chloride, rivastigmine, scopolamine, selegiline, testosterone, capsaicin, diclofenac epolamine, diclofenac sodium, lidocaine, methylphenidate, salicylic acid, rivastigmine, rotigotine, scopolamine, trolamine salicylate, a combination of estradiol and levonorgestrel, a combination of estradiol and norethindrone acetate, a combination of ethinyl estradiol and norelgestromin, a combination of lidocaine and prilocaine, a combination of lidocaine and tetracaine, a combination of menthol and capsaicin, and a combination of menthol and methyl salicylate.

8. The transdermal drug delivery system of claim 7, wherein the active pharmaceutical agent is naltrexone HCl and is administered in an amount in a range from about 10 to 100 mg/cm$^2$.

9. The transdermal drug delivery system of claim 8, wherein the naltrexone HCl is administered in an amount of 27 mg/cm$^2$.

10. A transdermal drug delivery system for transdermal delivery of an active pharmaceutical agent to microneedle-treated skin of a subject for up to 7 days, comprising:
 (a) a first topical formulation for one-time application to skin of the subject, comprising a pharmaceutically acceptable topical carrier and a lipid biosynthesis inhibitor compound;
 (b) a second topical formulation for a one-time application to skin of the subject, comprising a pharmaceutically acceptable topical carrier and an active pharmaceutical agent for transdermal delivery to the subject; and (c) optionally, a microneedle array which produces a plurality of micropores that breach at least the stratum corneum of the skin of the subject;

wherein the first topical formulation and the second topical formulation each independently are formulated to be administered to skin of the subject one time in 7 days before, after or during microneedle treatment of the skin to produce micropores that breach at least the stratum corneum of the skin, and wherein healing or resealing of the micropores in the microneedle-treated skin is delayed for longer than 72 hours and up to 7 days such that the transdermal drug delivery system delivers a pharmaceutically effective and sustained dose of the active pharmaceutical agent over a period of at least 72 hours.

11. The transdermal drug delivery system of claim 10, wherein the lipid biosynthesis inhibitor is selected from the group consisting of fatty acid synthesis inhibitors, cholesterol synthesis inhibitors and ceramide synthesis inhibitors.

12. The transdermal drug delivery system of claim 10, wherein the lipid biosynthesis inhibitor is selected from the group consisting of 5-(tetradecycloxy)-2-furancarboxylic acid (TOFA), HMG-CoA reductase inhibitors, and β-chloralanine (BCA).

13. The transdermal drug delivery system of claim 12, wherein the HMG-CoA reductase inhibitor is selected from a group consisting of: atorvastatin, fluvastatin, pitavastatin, pravastatin, rosuvastatin, and simvastatin.

14. The transdermal drug delivery system of claim 13, wherein the HMG-CoA reductase inhibitor is fluvastatin and is administered in an amount in a range from about 0.1 to 10 $mg/cm^2$.

15. The transdermal drug delivery system of claim 14, wherein the fluvastatin is administered in an amount of 0.6 $mg/cm^2$.

16. The transdermal drug delivery system of claim 10, wherein the active pharmaceutical agent is selected from the group consisting of buprenorphine, clonidine, estradiol, fentanyl, granisetron, methylphenidate, naltrexone HCl, nicotine, nitroglycerin, oxybutynin, oxybutynin chloride, rivastigmine, scopolamine, selegiline, testosterone, capsaicin, diclofenac epolamine, diclofenac sodium, lidocaine, methylphenidate, salicylic acid, rivastigmine, rotigotine, scopolamine, trolamine salicylate, a combination of estradiol and levonorgestrel, a combination of estradiol and norethindrone acetate, a combination of ethinyl estradiol and norelgestromin, a combination of lidocaine and prilocaine, a combination of lidocaine and tetracaine, a combination of menthol and capsaicin, and a combination of menthol and methyl salicylate.

17. The transdermal drug delivery system of claim 16, wherein the active pharmaceutical agent is naltrexone HCl and is administered in an amount in a range from about 10 to 100 $mg/cm^2$.

18. The transdermal drug delivery system of claim 17, wherein the naltrexone HCL is administered in an amount of 27 $mg/cm^2$.

19. The transdermal drug delivery system of claim 1, wherein the topical formulation is contained within a laminated structure that serves as a drug delivery device to be affixed to the skin.

20. The transdermal drug delivery system of claim 10, wherein the second topical formulation and optionally also the first topical formulation is contained within a laminated structure that serves as a drug delivery device to be affixed to the skin.

21. The transdermal drug delivery system of claim 10, wherein the first topical formulation is administered prior to the second topical formulation.

22. The transdermal drug delivery system of claim 1, wherein the transdermal drug delivery system delivers a pharmaceutically effective and sustained dose of the active pharmaceutical agent over a period of about 5 days.

23. The transdermal drug delivery system of claim 10, wherein the transdermal drug delivery system delivers a pharmaceutically effective and sustained dose of the active pharmaceutical agent over a period of about 5 days.

24. The transdermal drug delivery system of claim 1, wherein the transdermal drug delivery system delivers a pharmaceutically effective and sustained dose of the active pharmaceutical agent over a period of about 6 days.

25. The transdermal drug delivery system of claim 10, wherein the transdermal drug delivery system delivers a pharmaceutically effective and sustained dose of the active pharmaceutical agent over a period of about 6 days.

26. The transdermal drug delivery system of claim 1, wherein the transdermal drug delivery system delivers a pharmaceutically effective and sustained dose of the active pharmaceutical agent over a period of about 7 days.

27. The transdermal drug delivery system of claim 10, wherein the transdermal drug delivery system delivers a pharmaceutically effective and sustained dose of the active pharmaceutical agent over a period of about 7 days.

28. The transdermal drug delivery system of claim 1, wherein the topical formulation delivers a maximum dose of lipid biosynthesis inhibitor of 1.2 mg over 7 days to the subject.

29. The transdermal drug delivery system of claim 10, wherein the first topical formulation delivers a maximum dose of lipid biosynthesis inhibitor of 1.2 mg over 7 days to the subject.

* * * * *